(12) United States Patent
Kume et al.

(10) Patent No.: US 9,376,665 B2
(45) Date of Patent: Jun. 28, 2016

(54) METHOD FOR PRODUCING INTESTINAL CELLS

(75) Inventors: Shoen Kume, Kumamoto (JP); Soichiro Ogaki, Fukuoka (JP); Nobuaki Shiraki, Kumamoto (JP); Kazuhiko Kume, Kumamoto (JP)

(73) Assignees: National University Corporation Kumamoto University, Kumamoto-Shi (JP); LSIP, LLC, Tokyo (JP)

( * ) Notice: Subject to any disclaimer, the term of this patent is extended or adjusted under 35 U.S.C. 154(b) by 150 days.

(21) Appl. No.: 13/882,904

(22) PCT Filed: Oct. 31, 2011

(86) PCT No.: PCT/JP2011/075041
§ 371 (c)(1),
(2), (4) Date: Oct. 9, 2013

(87) PCT Pub. No.: WO2012/060315
PCT Pub. Date: May 10, 2012

(65) Prior Publication Data
US 2014/0199700 A1   Jul. 17, 2014

(30) Foreign Application Priority Data

Nov. 2, 2010   (JP) .................................. 2010-246161

(51) Int. Cl.
*C12N 5/071*   (2010.01)
*G01N 33/50*   (2006.01)
*C12Q 1/68*   (2006.01)

(52) U.S. Cl.
CPC ............ *C12N 5/0679* (2013.01); *C12Q 1/6881* (2013.01); *G01N 33/5064* (2013.01); *G01N 33/5073* (2013.01); *C12N 2501/115* (2013.01); *C12N 2501/117* (2013.01); *C12N 2501/119* (2013.01); *C12N 2501/16* (2013.01); *C12N 2501/415* (2013.01); *C12N 2501/42* (2013.01); *C12N 2501/999* (2013.01); *C12N 2502/13* (2013.01); *C12N 2506/02* (2013.01); *C12Q 2600/158* (2013.01); *G01N 2500/00* (2013.01)

(58) Field of Classification Search
CPC .................................................... C12N 5/0679
USPC ............................................................. 435/6
See application file for complete search history.

(56) References Cited

U.S. PATENT DOCUMENTS 5,942,435 A * 8/1999 Wheeler ....................... 435/325
2009/0004152 A1   1/2009 Martinson et al.

FOREIGN PATENT DOCUMENTS

| CN | 101365784 A | 2/2009 |
|---|---|---|
| WO | WO-2006-126574 A1 | 11/2006 |
| WO | WO-2007-050043 A2 | 5/2007 |
| WO | WO-2008-013664 A2 | 1/2008 |
| WO | WO-2010-011352 A2 | 1/2010 |
| WO | WO-2010-051223 A1 | 5/2010 |
| WO | WO-2010-108005 A2 | 9/2010 |
| WO | WO-2011-140441 A2 | 11/2011 |

OTHER PUBLICATIONS

Ueda et al.*
Inami et al., 2010, Immunology and Cell Biology, pp. 1-8.*
McLean et al., 2007, Stem Cells, vol. 25, pp. 29-38.*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Goddard et al., 1997, J. Nutr., vol. 127, pp. 177-183.*
Zecchini, et al., "Notch Signaling Regulates the Differentiation of Post-Mitotic Intestinal Epithelial Cells", *Genes Dev.*, 2005, 19: 1686-1691.
English translation of International Preliminary Report on Patentability of Chapter I, i.e., International Search Opinion, issued in PCT/JP2011/075041 on May 23, 2013.
Japanese version of International Preliminary Report on Patentability of Chapter I, i.e., International Search Opinion, issued in PCT/JP2011/075041 on May 16, 2013.
Ishikawa et al "Characterization of in vitro gut-like organ formed from mouse embryonic stem cells." *Am J. Physio Cell Physio* 286: C1344-C1352, 2004.
Matsuura et al, "Crucial Transcription Factors in Endoderm and Embryonic Gut Development are Expressed in Gut-Like Structures from mouse ES Cells." *Stem Cells* 2006; 24: 624-630.
Torihashi et al, "Gut-Like Structures from Mouse Embryonic Stem Cells as an In Vitro Model for Gut Organogenesis Preserving Developmental Potential After Transplantation." *Stem Cells* 2006; 24: 2618-2626.
Ueda et al, "Generation of functional gut-like organ from mouse induced pluripotent stem cells." *Biochemical and Biophysical Research Communications.* 391 (2010) 38-42.
D'Amour, et al. "Efficient differentiation of human embryonic stem cells to definitive endoderm", *Nature Biotechnology* (2005) pp. 1534-1541.

(Continued)

*Primary Examiner* — Anoop Singh
*Assistant Examiner* — David A Montanari
(74) *Attorney, Agent, or Firm* — Mintz Levin Cohn Ferris Glovsky and Popeo, P.C.; David G. Conlin; Joohee Lee

(57) ABSTRACT

An object of the present invention is to provide a method of producing intestinal cells by use of pluripotent stem cells as a starting material. According to the present invention, provided is a method of producing intestinal cells, comprising the steps of: (A) inducing differentiation of pluripotent stem cells into definitive endoderm cells; and (B) culturing the definitive endoderm cells in the presence of (2'Z,3'E)-6-bromoindirubin-3'-oxime (BIO) and N-[(3,5-difluorophenyl)acetyl]-L-Ala-2-phenyl-L-Gly-tert-butyl-OH (DAPT) to thereby induce differentiation of the definitive endoderm cells into intestinal cells.

4 Claims, 10 Drawing Sheets

(56) References Cited

OTHER PUBLICATIONS

Nakamura, et al. "Crosstalk between Wnt and Notch signaling in intestinal epithelial cell fate decision", *Journal of Gastroenterology*, (2007) 705-710.

Shiraki et al. "Differentiation of mouse and human embryonic stem cells into hepatic lineages", Genes to Cells (2008), p. 731-746.

Shiraki, et al. "Guided differentiation of embryonic stem cells into Pdx1-expressing regional-specific definitive endoderm", *Stem Cells* (2008) 874-885.

Supplementary European Search Report in EP11837965.0 issued Mar. 28, 2014.

van Es, et al. "Notch/γ-secretase inhibition turns proliferative cells in intestinal crypts and adenomas into goblet cells", *Nature*, (2005) p. 959-963.

* cited by examiner

SEQUENCE LISTING

```
<160> NUMBER OF SEQ ID NOS: 54

<210> SEQ ID NO 1
<211> LENGTH: 27
<212> TYPE: DNA
<213> ORGANISM: Artificial
<220> FEATURE:
<223> OTHER INFORMATION: Description of Artificial Sequence: Synthetic
      DNA

<400> SEQUENCE: 1
tgcctttccc catgctgcct ccgtgta                                           27

<210> SEQ ID NO 2
<211> LENGTH: 29
<212> TYPE: DNA
<213> ORGANISM: Artificial
<220> FEATURE:
<223> OTHER INFORMATION: Description of Artificial Sequence: Synthetic
      DNA

<400> SEQUENCE: 2
ggtgggtggt gcgcttggcc ttgatgtag                                         29

<210> SEQ ID NO 3
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 3
tggtgtacac agaccatcag c                                                 21

<210> SEQ ID NO 4
<211> LENGTH: 18
<212> TYPE: DNA
<213> ORGANISM: Artificial
<220> FEATURE:
<223> OTHER INFORMATION: Description of Artificial Sequence: Synthetic
      DNA

<400> SEQUENCE: 4
ccttggctct gcggttct                                                     18

<210> SEQ ID NO 5
<211> LENGTH: 22
<212> TYPE: DNA
```

<213> ORGANISM: Artificial
<220> FEATURE:
<223> OTHER INFORMATION: Description of Artificial Sequence: Synthetic DNA

<400> SEQUENCE: 5
ggaaaggagc tgattgctgt cc       22

<210> SEQ ID NO 6
<211> LENGTH: 22
<212> TYPE: DNA
<213> ORGANISM: Artificial
<220> FEATURE:
<223> OTHER INFORMATION: Description of Artificial Sequence: Synthetic DNA

<400> SEQUENCE: 6
ctttgacaag gctggagacc ag       22

<210> SEQ ID NO 7
<211> LENGTH: 20
<212> TYPE: DNA
<213> ORGANISM: Artificial
<220> FEATURE:
<223> OTHER INFORMATION: Description of Artificial Sequence: Synthetic DNA

<400> SEQUENCE: 7
agtttgccca gaccacaaag       20

<210> SEQ ID NO 8
<211> LENGTH: 20
<212> TYPE: DNA
<213> ORGANISM: Artificial
<220> FEATURE:
<223> OTHER INFORMATION: Description of Artificial Sequence: Synthetic DNA

<400> SEQUENCE: 8
cagggtaatg ggtgaagtgg       20

<210> SEQ ID NO 9
<211> LENGTH: 20
<212> TYPE: DNA
<213> ORGANISM: Artificial
<220> FEATURE:
<223> OTHER INFORMATION: Description of Artificial Sequence: Synthetic DNA

<400> SEQUENCE: 9
gtctcccagc ctcatgtttc       20

<210> SEQ ID NO 10
<211> LENGTH: 22
<212> TYPE: DNA
<213> ORGANISM: Artificial
<220> FEATURE:
<223> OTHER INFORMATION: Description of Artificial Sequence: Synthetic DNA

<400> SEQUENCE: 10
tggaaccaaa tcttcacttg tc       22

<210> SEQ ID NO 11
<211> LENGTH: 20
<212> TYPE: DNA
<213> ORGANISM: Artificial

```
<220> FEATURE:
<223> OTHER INFORMATION: Description of Artificial Sequence: Synthetic
      DNA

<400> SEQUENCE: 11
gttatgagcc cgaaagtgga                                                    20

<210> SEQ ID NO 12
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 12
agagaaggca gctggagtca                                                    20

<210> SEQ ID NO 13
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 13
cccatcttca aaaacggaga                                                    20

<210> SEQ ID NO 14
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 14
ccctatcggc atcaaaagac                                                    20

<210> SEQ ID NO 15
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 15
gtgatggtgg gaatgggtca                                                    20

<210> SEQ ID NO 16
<211> LENGTH: 22
<212> TYPE: DNA
<213> ORGANISM: Artificial
<220> FEATURE:
<223> OTHER INFORMATION: Description of Artificial Sequence: Synthetic
      DNA

<400> SEQUENCE: 16
tttgatgtca cgcacgattt cc                                                 22

<210> SEQ ID NO 17
<211> LENGTH: 19
<212> TYPE: DNA
<213> ORGANISM: Artificial
<220> FEATURE:
```

```
<223> OTHER INFORMATION: Description of Artificial Sequence: Synthetic
      DNA

<400> SEQUENCE: 17
catcctgtgc agtggtcct                                                19

<210> SEQ ID NO 18
<211> LENGTH: 19
<212> TYPE: DNA
<213> ORGANISM: Artificial
<220> FEATURE:
<223> OTHER INFORMATION: Description of Artificial Sequence: Synthetic
      DNA

<400> SEQUENCE: 18
gcaccataca ttggcttgg                                                19

<210> SEQ ID NO 19
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 19
gagaccgaag caccgactat g                                             21

<210> SEQ ID NO 20
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 20
cggttttgac attgtgttcg c                                             21

<210> SEQ ID NO 21
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 21
ccgtcagttt ctgcagaagt                                               20

<210> SEQ ID NO 22
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 22
cagggtcaag ttgagcatcg                                               20

<210> SEQ ID NO 23
<211> LENGTH: 20
<212> TYPE: DNA
<213> ORGANISM: Artificial
<220> FEATURE:
<223> OTHER INFORMATION: Description of Artificial Sequence: Synthetic
```

DNA

<400> SEQUENCE: 23
gttgcagcat ttgtcacacc                                          20

<210> SEQ ID NO 24
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 24
tgaacgatca acagcagacc                                          20

<210> SEQ ID NO 25
<211> LENGTH: 22
<212> TYPE: DNA
<213> ORGANISM: Artificial
<220> FEATURE:
<223> OTHER INFORMATION: Description of Artificial Sequence: Synthetic
      DNA

<400> SEQUENCE: 25
ggttccggag tgggcaggtt tg                                       22

<210> SEQ ID NO 26
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 26
ggggcgtggg gtggaatcag                                          20

<210> SEQ ID NO 27
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 27
accaatgagg acctggaaca                                          20

<210> SEQ ID NO 28
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 28
tcctactggt cttcctcagc a                                        21

<210> SEQ ID NO 29
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 29
atgaagagcg gcgtatgtct                                                20

<210> SEQ ID NO 30
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 30
cgatgggtat tcgtagtcct c                                              21

<210> SEQ ID NO 31
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 31
ggaacctgtg cgagtggatg                                                20

<210> SEQ ID NO 32
<211> LENGTH: 23
<212> TYPE: DNA
<213> ORGANISM: Artificial
<220> FEATURE:
<223> OTHER INFORMATION: Description of Artificial Sequence: Synthetic
      DNA

<400> SEQUENCE: 32
aggtggtggg gcttgcgggg gcg                                            23

<210> SEQ ID NO 33
<211> LENGTH: 19
<212> TYPE: DNA
<213> ORGANISM: Artificial
<220> FEATURE:
<223> OTHER INFORMATION: Description of Artificial Sequence: Synthetic
      DNA

<400> SEQUENCE: 33
acttctatgg gggcgactg                                                 19

<210> SEQ ID NO 34
<211> LENGTH: 19
<212> TYPE: DNA
<213> ORGANISM: Artificial
<220> FEATURE:
<223> OTHER INFORMATION: Description of Artificial Sequence: Synthetic
      DNA

<400> SEQUENCE: 34
atgcgtccct tgaagatgg                                                 19

<210> SEQ ID NO 35
<211> LENGTH: 28
<212> TYPE: DNA
<213> ORGANISM: Artificial
<220> FEATURE:
<223> OTHER INFORMATION: Description of Artificial Sequence: Synthetic
      DNA

```
<400> SEQUENCE: 35
gataaactaa aagcataggc tgcatatg                                       28

<210> SEQ ID NO 36
<211> LENGTH: 26
<212> TYPE: DNA
<213> ORGANISM: Artificial
<220> FEATURE:
<223> OTHER INFORMATION: Description of Artificial Sequence: Synthetic
      DNA

<400> SEQUENCE: 36
tcaaaatcag aatggcaatt atctct                                         26

<210> SEQ ID NO 37
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 37
caggaggctc tgagaggaca                                                20

<210> SEQ ID NO 38
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 38
atctgtgcag aagggatgct                                                20

<210> SEQ ID NO 39
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 39
gctgcaccgt tagagatgac                                                20

<210> SEQ ID NO 40
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 40
cggtttttgc tcccttaaca                                                20

<210> SEQ ID NO 41
<211> LENGTH: 19
<212> TYPE: DNA
<213> ORGANISM: Artificial
<220> FEATURE:
<223> OTHER INFORMATION: Description of Artificial Sequence: Synthetic
      DNA

<400> SEQUENCE: 41
```
cccaaggagt gcaacaacc                                              19

<210> SEQ ID NO 42
<211> LENGTH: 21
<212> TYPE: DNA
<213> ORGANISM: Artificial
<220> FEATURE:
<223> OTHER INFORMATION: Description of Artificial Sequence: Synthetic
      DNA

<400> SEQUENCE: 42
gggacagaaa agctgagatg a                                           21

<210> SEQ ID NO 43
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 43
gatggctaca ggggaatcag                                             20

<210> SEQ ID NO 44
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 44
taactgctcc tggggttttg                                             20

<210> SEQ ID NO 45
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 45
tggctggagg aagaagaaga                                             20

<210> SEQ ID NO 46
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 46
tcagtttttc aggggacagg                                             20

<210> SEQ ID NO 47
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 47

-continued ctccactcct cccaactctg                                          20

<210> SEQ ID NO 48
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 48
actccacacc tcctctccaa                                          20

<210> SEQ ID NO 49
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 49
gatgctgtcc tgccgcctcc                                          20

<210> SEQ ID NO 50
<211> LENGTH: 18
<212> TYPE: DNA
<213> ORGANISM: Artificial
<220> FEATURE:
<223> OTHER INFORMATION: Description of Artificial Sequence: Synthetic
      DNA

<400> SEQUENCE: 50
tgccatagcc gggtttga                                            18

<210> SEQ ID NO 51
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 51
gcagatacct cctactacca                                          20

<210> SEQ ID NO 52
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 52
gaagcaggag tctacacagt                                          20

<210> SEQ ID NO 53
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 53
cgagatccct ccaaaatcaa                                          20

```
<210> SEQ ID NO 54
<211> LENGTH: 23
<212> TYPE: DNA
<213> ORGANISM: Artificial
<220> FEATURE:
<223> OTHER INFORMATION: Description of Artificial Sequence: Synthetic
      DNA

<400> SEQUENCE: 54
catgagtcct tccacgatac caa                                              23
```

METHOD FOR PRODUCING INTESTINAL CELLS

TECHNICAL FIELD

The present invention relates to a method of producing intestinal cells. More particularly, the present invention relates to a method of producing intestinal cells by use of pluripotent stem cells as a starting material.

BACKGROUND ART

Pluripotent stem cells such as embryonic stem cells (ES cells) or induced pluripotent stem cells (iPS cells) are cells having a capability of differentiating into various cells, and they possess a capability of almost indefinitely proliferating. Recently, particularly in the field of regenerative medicine, there has been a need for development of methods which produce, by use of such pluripotent stem cells as a starting material, tissues and cells applicable to various organs such as stomach, pancreas, liver and intestine. More specifically, as the survival rate of premature babies has rapidly increased due to advancements of neonatal medicine, there is an increased need for a regeneration medicinal technology which is effective to infants with congenital hypoplasia in digestive tracts. Furthermore, since epithelial metaplasia in intestines, or irreversible structural changes in gastrointestinal mucous membranes occur in gastrointestinal malignant tumors, stricture or fibrosis developed after surgeries for said disease, reflux esophagitis, and digestive-tract dysfunction due to tissue destruction that is involved in chronic inflammatory intestinal diseases such as ulcerative colitis and Crohn disease, there has been a need for regenerative-medicine-based therapies therefor. In order to realize regenerative-medicine-based therapies against such digestive system disorders, there has been a urgent need to develop an efficient method of producing intestinal cells by use of pluripotent stem cells as a starting material.

With regard to methods of differentiating embryonic stem cells into endodermal cells, for example, a method in which mesoderm-derived cells are used as feeder cells, and embryonic stem cells are cultured in the presence of said feeder cells to thereby induce differentiation of them into endodermal cells (see WO2006/126574). The patent document WO2006/126574 describes induction of differentiation thereof into mature cells of endoderm-derived organs such as liver, lung, and small intestine, but the disclosed method cannot efficiently differentiate the cells into various matured intestinal cells.

Moreover, techniques have been established, in which ES cells are culture on a monolayer of M15 cells in vitro to thereby induce the ES cells sequentially into the mesendoderm, the definitive endoderm, and, finally, various organs derived from the regional-specific definitive endoderm, as they mimic in vivo induction of early embryos [see Shiraki, N., Umeda, K., Sakashita, N., Takeya, M., Kume, K. and Kume, S. (2008). Differentiation of mouse and human embryonic stem cells into hepatic lineages. Genes Cells 13, 731-46; and Shiraki, N., Yoshida, T., Araki, K., Umezawa, A., Higuchi, Y., Goto, H., Kume, K. and Kume, S. (2008b). Guided differentiation of embryonic stem cells into Pdx1-expressing regional-specific definitive endoderm. Stem Cells 26, 874-851. It has been confirmed that these techniques have succeeded in inducing differentiation of the ES cells into hepatic cells, pulmonary cells, pancreatic cells and the like. Particularly, the document of Shiraki et al (2008b) describes that Cdx2-expressing intestinal precursor cells also were generated besides hepatic, pulmonary, and pancreatic cells. However, it is difficult to produce various types of more mature intestinal cells massively and effectively by use of these conventional arts.

As described above, techniques for inducing differentiation of pluripotent stem cells into various types of mature intestinal cells massively and effectively still remain to be developed. At present, any efficient methods of producing intestinal cells by use of pluripotent stem cells as a starting material do not exist.

SUMMARY OF THE INVENTION

An object of the present invention is to provide a method of producing intestinal cells by use of pluripotent stem cells as a starting material.

The present inventors conducted extensive studies to solve the above-mentioned problem, and, as a result, the present inventors discovered that, after inducing differentiation of embryonic stem cells, which are pluripotent stem cells, into definitive endoderm cells, the definitive endoderm cells be cultured in the presence of BIO [(2'Z,3'E)-6-bromoindirubin-3'-oxime] and DAPT [N-[(3,5-difluorophenyl)acetyl]-L-Ala-2-phenyl-L-Gly-tert-butyl-OH], whereby differentiation thereof into various mature intestinal cells can be induced. This discovery resulted in completion of the present invention.

That is to say, the present invention relates to the followings.

(1) A method of producing intestinal cells, comprising the steps of:
(A) inducing differentiation of pluripotent stem cells into definitive endoderm cells; and (B) culturing the definitive endoderm cells in the presence of (2'Z,3'E)-6-bromoindirubin-3'-oxime (BIO) and N-[(3,5-difluorophenyl)acetyl]-L-Ala-2-phenyl-L-Gly-tert-butyl-OH (DAPT) to thereby induce differentiation of the definitive endoderm cells into intestinal cells.

(2) The method according to (1), wherein the definitive endoderm cells are separated from a cell culture obtained in step (A) by flow cytometry using fluorescently-labelled antibodies against E-cadherin (ECD) and CXCR4, and said separated definitive endoderm cells are used in the step (B).

(3) The method according to (1) or (2), wherein, in step (A), the pluripotent stem cells are cultured in the presence of feeder cells and in the presence of activin and/or bFGF to thereby induce of differentiation of the pluripotent stem cells into the definitive endoderm cells.

(4) The method according to (3), wherein the feeder cells are cells derived from a mesoderm.

(5) The method according to (3) or (4), wherein the feeder cells are M15 cells, MEF cells, or ST2 cells.

(6) The method according to any one of (1) to (5), wherein the definitive endoderm cells are cultured in the presence of M15 cells or MEF cells in step (B).

(7) The method according to any one of (1) to (6), wherein the pluripotent stem cells are embryonic stem cells or induced pluripotent stem cells.

(8) The method according to any one of (1) to (7), wherein the pluripotent stem cells are human embryonic stem cells or mouse embryonic stem cells.

(9) Intestinal cells which are obtained by inducing differentiation of pluripotent stem cells and which are obtained by the method according to any one of (1) to (8).

(10) A method of screening for substances which promote or inhibit induction of differentiation of pluripotent stem cells into intestinal cells, the method comprising: culturing pluripotent stem cells in the presence of a test substance in inducing differentiation of the pluripotent stem cells into intestinal cells by the method according to any one of (1) to (8); and comparing a level of differentiation of the pluripotent stem cells into intestinal cells in a case where the pluripotent stem cells are cultured in the presence of the test substance with a level of differentiation of pluripotent stem cells into intestinal cells in a case where the pluripotent stem cells are cultured in the absence of the test substance.

(11) The screening method according to (10), wherein the test substance is a growth factor or a low-molecular-weight compound.

(12) The screening method according to (10) or (11), wherein an amount of maker transcript or a protein thereof expressed in intestinal cells, or both of them are used as indicators to thereby determine the levels of differentiation into intestinal cells.

According to the production method of the present invention, various mature intestinal cells, such as absorptive enterocytes of the intestine, Paneth cells, goblet cells and enteroendocrine cells, can be produced massively and efficiently from pluripotent stem cells. According to the present invention, as described above, various mature intestinal cells can be produced, and the produced cells can be practically utilized in the field of regeneration medicine.

BRIEF DESCRIPTION OF THE DRAWINGS

In FIG. 1D, "FI" represents fetal intestine; "AI" represents adult intestine; and "DW" represents a negative control without cDNA. Intestinal markers Cdx2 and Villin; and enterocyte markers Ifabp, Isx, and lactase were induced in the ES cells which had been differentiated in the presence of BIO and DAPT and on M15 cells.

FIG. 4A shows that intestinal cells derived from the ES cells are Cdx2/ECD/HNF4a-positive cells. FIG. 4B shows that these cells also express Glut2. FIG. 4C shows that a population of said cells expressed Claudin7. FIG. 4D shows that Paneth cells (Lysozyme expression) and cells expressing endocrine markers [Chromogranin A (Chga) and Somatostatin (sst)] are induced therein.

FIG. 5E shows that Mucin2/DBA-expressing cells were also induced therein. FIG. 5F shows that Sox9-expressing cells existed within the villin-expressing cells. FIG. 5G shows that enterocytes (with alkaline phosphatase activities) were induced therein. FIGS. 5H and 5I show that goblet cells (positive for PAS and Alucian blue staining) were also induced therein.

FIG. 7A shows results obtained by carrying out RT-PCR analysis with differentiated cells at day 15. FIG. 7B shows results of immunohistochemistry which was carried on differentiation day 12. FIGS. 7C and 7D show results of an RT-PCR analysis (C) and an immunohistochemistry analysis with anti-Cdx2 antibody (D) on expression of Cdx2 in differentiated ES cells on day 12. In the experiment regarding the results of FIG. 7, the ES cells were cultured on M15 with activin and bFGF for 4 days, and then, culturing on M15 (FIG. 7A) or MEF (FIGS. 7B, 7C and 7D), with control (2000KSR) or at the presence of BIO and DAPT (BIO&DAPT), and with or without inhibitors (SU5402, LY29402 or U0126) was continued until Day 12.

EMBODIMENT FOR CARRYING OUT THE INVENTION

Figure 1:
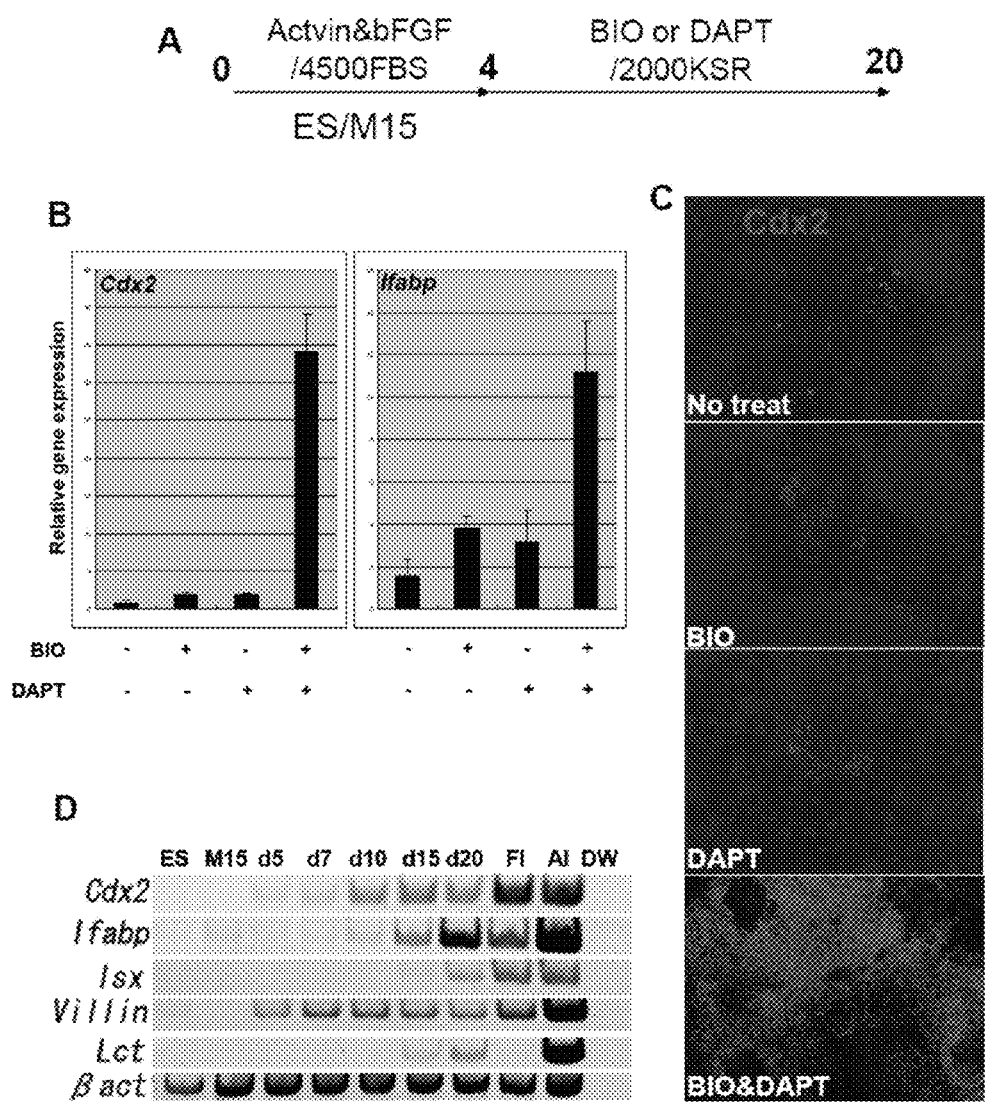
FIG. 1A is a schematic drawing of the experimental design. The ES cells were first cultured on the M15 in the presence of activin and bFGF, and then, and then, activin and bFGF were switched to BIO and DAPT, and the cells were further cultured until differentiation day 20, thereby inducing differentiation of the cells into definitive endoderm.
FIG. 1B shows results of real-time PCR analysis with respect to the ES cells which were differentiated on M15 and with BIO and DAPT added at different combinations (differentiation day 12). The combinations of BIO and DAPT simultaneously potentiate the expression of intestinal precursor cell markers, Cdx2 and Ifabp.
FIG. 1C shows photo of the differentiated ES cells at day 20, which were immune-stained with an anti-Cdx2 antibody. It is shown therein that a high proportion of ES cells be turned into Cdx2-expressing cells in the presence of BIO and DAPT, when grown on M15 cells.
FIG. 1D shows results of RT-PCR analysis of time-dependent expression of various intestinal markers with respect to the ES cells cultured on M15 cells and in the presence of BIO and DAPT.

The method of producing intestinal cells according to the present invention includes the steps of: (A) inducing differentiation of pluripotent stem cells into definitive endoderm cells; and (B) culturing the definitive endoderm cells in the presence of (2'Z,3'E)-6-bromoindirubin-3'-oxime (BIO) and N-[(3,5-difluorophenyl)acetyl]-L-Ala-2-phenyl-L-Gly-tert-butyl-OH (DAPT) to thereby induce differentiation of the definitive endoderm cells into intestinal cells.

In the present invention, "pluripotent stem cells" means cells which have a capability of proliferating under artificially-created conditions such as in a test tube (in vitro) and which can differentiate into cells found in all the tissues of living bodies. In the present invention, embryonic stem cells or induced pluripotent stem cells are preferably used as the pluripotent stem cells, and embryonic stem cells are more preferably used.

(Embryonic Stem Cells)

The embryonic stem (ES) cells used in the present invention may be mammalian-derived ES cells, and the types thereof are not particularly limited. For example, ES cells derived from a mouse, monkey, human, or the like can be used. With regard to the ES cells, for example, cells into which a reporter gene is introduced in the vicinity of the Pdx1 gene can be used in order to facilitate confirmation of the level of their differentiation. For example, a 129/Sv-derived ES cell line in which the LacZ gene is introduced into the Pdx1 locus, or a ES cell line SK7, having the GFP reporter transgene under the control of the Pdx1 promoter can be used. Alternatively, a ES cell line PH3, having the mRFP1 reporter transgene under the control of the Hnf3β-endoderm-specific-enhancer fragment and having the GFP reporter transgene under the controlled of the Pdx1 promoter also can be used. Moreover, in the present invention, with regard to those derived from mice, the mouse ES cell line R1 can be used while, with regard to those derived from humans, human ES cell lines KhES-1, KhES-2, and KhES-3 can be used. Among them, the mouse ES cell line R1 or the human ES cell line KhES-3 can be preferably used.

With regard to methods of culturing mammalian-derived ES cells, any ordinarily method can be adopted, and for example, the cells can be maintained in the Glasgow Minimum Essential Medium (Invitrogen) containing 1,000 units/mL of leukemia inhibitory factor (LIF; Chemicon), 15% Knockout Serum Replacement (KSR; Gibco), 1% Fetal Bovine Serum (FBS; Hyclone), 100 μM of Nonessential Amino Acid (NEAA; Invitrogen), 2 mM of L-glutamine (L-Gln; Invitrogen), 1 mM of sodium pyruvate (Invitrogen), 50 units/mL of penicillin and 50 μg/mL of streptomycin (PS; Invitrogen), and 100 μM of β-mercaptoethanol β-ME; Sigma).

(Induced Pluripotent Stem Cell)

The induced pluripotent stem cells (iPS cells) used in the present invention can be prepared by way of reprogramming somatic cells. The somatic cells used therein are not particularly limited to certain types, and any somatic cells can be used. That is, the somatic cells as referred to as in the present invention include all cells, other than germ cells, among cells constituting living bodies, and any differentiated somatic cells or undifferentiated stem cells are eligible. The somatic cells may be any of those derived from mammals, birds, fishes, reptiles and amphibians, and are not particularly limited. However, they are preferably those derived from mammals (e.g. rodents such as mice or primates such as humans), and particularly preferably those derived from mice or humans. Furthermore, if human somatic cells are used, those derived from any of fetuses, newborn infants and adults may be used.

The iPS cells in the present invention are referred to as stem cells having self-renewal capability over an extended period of time under predetermined culturing conditions (such as conditions where ES cells are cultured) and having pluripotency into the ectoderm, the mesoderm, and the endoderm under predetermined conditions for differentiation. In addition, the induced pluripotent stem cells in the present invention may be stem cells having an ability to form teratomas when they are implanted into a test animal such as a mouse.

In order to prepare iPS cells from somatic cells, at first, at least one or more reprogramming genes are introduced into the somatic cells. The reprogramming gene is a gene coding for a reprogramming factor that has an activity to reprogram somatic cells to form into iPS cells. Specific examples of combinations of reprogramming genes include the following combinations, but the combinations are not limited thereto.
(i) the Oct gene, the Klf gene, the Sox gene, and the Myc gene;
(ii) the Oct gene, the Sox gene, the NANOG gene, and the LIN28 gene;

(iii) the Oct gene, the Klf gene, the Sox gene, the Myc gene, the hTERT gene, and the SV40 large T gene; and
(iv) the Oct gene, the Klf gene, and the Sox gene.

The Oct gene, the Klf gene, the Sox gene and the Myc gene include their respective plural family genes. With regard to specific examples of their respective family genes, those described in pages 11 to 13 of the specification of International Publication No. WO 2007/069666 can be used. Specifically, they are as follows.

With regard to specific examples of genes belonging to the Oct gene, Oct3/4 (NM_002701), Oct1A (NM_002697), Oct6 (NM_002699) and the like can be mentioned (those in the parentheses indicate NCBI accession numbers for human genes). Preferable one is Oct3/4. Oct3/4 is a transcription factor belonging to the POU family, and is known as an undifferentiation marker, and there has been a report that Oct3/4 be involved in maintenance of pluripotency.

With regard to specific examples of genes belonging to the Klf gene, Klf1 (NM_006563), Klf2 (NM_016270), Klf4 (NM_004235), Klf5 (NM_001730) and the like can be mentioned (those in the parentheses indicate NCBI accession numbers for human genes). Preferable on is Klf4. Klf4 (Kruppel like factor-4) has been reported as a tumor inhibitory factor.

With regard to specific examples of genes belonging to the Sox gene for example, Sox1 (NM_005986), Sox2 (NM_003106), Sox3 (NM_005634), Sox7 (NM_031439), Sox15 (NM_006942), Sox17 (NM_0022454), and Sox18 (NM_018419) can be mentioned (those in the parentheses indicate NCBI accession numbers for human genes). Preferable one is Sox2. Sox2 is expressed in an early development process, and is a gene coding for a transcription factor.

With regard to specific examples of genes belonging to the Myc gene, c-Myc (NM_002467), N-Myc (NM_005378), L-Myc (NM_005376) and the like can be mentioned (those in the parentheses indicate NCBI accession numbers for human genes). Preferable one is c-Myc. c-Myc is a transcriptional regulator that is involved in differentiation and proliferation of cells, and there has been a report that c-Myc be involved in maintenance of pluripotency.

The above-mentioned genes are genes which commonly exist in mammals including humans, and genes derived from any mammals (e.g. derived from mammals such as humans, mice, rats, and monkeys) can be used in the present invention. In addition, a mutant gene in which several nucleotides (e.g. 1 to 30, preferably 1 to 20, more preferably 1 to 10, yet more preferably 1 to 5, particularly preferably 1 to 3) are substituted, inserted and/or deleted with respect to the wild-type gene and which has the same function as the wild-type gene can also be used.

In the present invention, as reprogramming genes, the combination of the Oct3/4 gene, the Klf4 gene, the Sox2 gene, and the c-Myc gene can be particularly preferably used.

A method for introducing reprogramming genes into somatic cells is not particularly limited as long as the introduced reprogramming genes can be expressed therein to thereby achieve reprogramming of somatic cells. For example, an expression vector containing at least one or more reprogramming genes can be used to introduce the reprogramming genes into somatic cells. When two or more reprogramming genes are introduced into somatic cells by use of a vector, said two or more genes may be integrated into one expression vector, and said expression vector may be introduced into somatic cells; or said two or more expression vectors, into each of which one reprogramming gene is inserted, may be prepared, and these may be introduced into somatic cells.

Types of expression vectors are not particularly limited, and the expression vectors may be virus vectors or plasmid vectors. However, virus vectors are preferable, and a virus vector that integrates inserted reprogramming genes into chromosomes of somatic cells is particularly preferable. With regard to virus vectors applicable to the present invention, retrovirus vectors (including lentivirus vectors), adenovirus vectors, adeno-associated virus vectors, and the like can be mentioned. Among the above-mentioned vectors, retrovirus vectors are preferable, and lentivirus vectors are particularly preferable.

With regard to packaging cells used for preparing recombinant virus vectors, any cells can be used as long as the cells can compensate for a deficient protein of gene, which is deficient in the recombinant virus vector plasmid and which is at least one of genes required for viral packaging. For example, packaging cells based on human-kidney-derived cells HEK293 or mouse fibroblast cells NIH3T3 can be used.

The recombinant virus vectors can be prepared by way of introducing a recombinant virus vector plasmid into packaging cells. A method used for introducing the virus vector plasmid into the above-mentioned packaging cells is not particularly limited, and said introduction can be carried out by any known techniques for gene introduction, such as the calcium phosphate method, the lipofection method or the electroporation method.

Culture media which can maintain undifferentiation and pluripotency of ES cells have been heretofore known in the art, and the induced pluripotent stem cells of the present invention can be separated and cultured by using suitable media in combination. That is, with regard to culture media used for culturing the induced pluripotent stem cells of the present invention, an ES culture medium; an MEF-conditioned ES culture medium that is a culture supernatant obtained by way of adding 10 ng/mL of EGF-2 (bFGF) to an ES culture medium and then culturing mouse embryonic fibroblasts therein for 24 hours (hereinafter referred to as "MEF-conditioned ES culture medium"); and the like can be mentioned. To culture media used for culturing the induced pluripotent stem cells of the present invention may be added various growth factors, cytokines, hormones and the like (e.g. components involved in proliferation/maintenance of human ES cells, such as FGF-2 (bFGF), TGFb-1, Activin A, Noggin, BDNF, NGF, NT-1, NT-2, and NT-3). In addition, differentiation potency and proliferation potency of separated induced pluripotent stem cells can be confirmed by any known confirmation means for ES cells.

(Induction of Differentiation of Pluripotent Stem Cells into Definitive Endoderm Cells)

The term "definitive endoderm cells" (definitive endoderm) in the present invention means cells which can differentiate into all gastrointestinal tracts including esophagus, stomach, small intestine and large intestine, as well as intestinal-tract-derived organs such as lung, liver, thymus, parathyroid gland, thyroid gland, gallbladder, or pancreas, and specifically refers to endoderm cells which are positive for E-cadherin (ECD) and CXCR4, or E-cadherin and CD55, serving as their marker genes (Shiraki N, Harada S, Ogaki S, Kume K. and Kume S. Identification of DAF1/CD55, a novel definitive endoderm marker. Cell Struct. Funct. 35, 73-80, 2010; Japanese Patent Application No. 2009-225758).

In the present invention, Step (A) of inducing differentiation of pluripotent stem cells into definitive endoderm cells is not particularly limited, and can be carried out by various known methods. For example, the method described in Japanese Patent Publication No. 2007-516728 (Published Japanese Translation of the PCT International Publication), etc. can be used, but a preferable method will be explained below.

In Step (A) of the present invention, the above-mentioned pluripotent stem cells can be cultured in the presence of appropriate feeder cells and in the presence of activin and/or a basic fibroblast growth factor (bFGF) to thereby induce differentiation thereof into desired definitive endoderm cells.

The above-mentioned feeder cells used in the present invention are not particularly limited as long as the cells can induce differentiation of the pluripotent stem cells into definitive endoderm cells. However, mesoderm-derived cells can be preferably used as the feeder cells. With regard to specific examples of such feeder cells, M15 cells, MEF cells, ST2 cells and the like can be mentioned. In addition, those which has been caused to lose their cell proliferation by a Mitomycin C treatment or exposure to radiation can be used as the feeder cells.

M15 cells (mouse, mesonephros) used in the present invention has been registered as Registration No. ECACC 95102517 in Cell Bank [CAMR Centre for Applied Microbiology & Research (ECACC, Salisbury, Wiltshire)]. The M15 cells can be obtained in accordance with the description of the reference [Larsson, S. H., Charlieu, J. P., Miyagawa, K., et al. (1995). Subnuclear localization of WT1 in splicing or transcription factor domains is regulated by alternative splicing. Cell 81, 391-401]. The bank information of M15 cells will be described below.
Version 4.200201
M15 (mouse, mesonephros)
ECACC 95102517
Morphology: Epithelial
Mouse mesonephric epithelium, polyoma virus large T transformed
Depositor: Prof V van Heyningen, MRC Human Genetics Unit, Western General Hospital, Edinburgh, UK (Originator)
No restrictions. Patent: None Specified By Depositor
Properties: Products: WT1 (expressed gene) Applications: Gene expression and protein studies connected to kidney development and Wilms' tumourigenesis.
Available in the following LABORATORY:
CAMR Centre for Applied Microbiology & Research (ECACC, Salisbury, Wiltshire) DMEM+2 mM Glutamine+ 10% Fetal Bovine Serum (FBS). Split confluent cultures 1:5 to 1:10 i.e. seeding at 5×1,000 to 1×10,000 cells/cm2 using 0.25% trypsin or trypsin/EDTA; 5% CO2; 37 C [cell growth impaired at lower densities]. Karyotype: Hyperdiploid
Hazard: CZ-II
The WT1-expressing mesonephric cell line M15 (alias Meso15) was established from mouse mesonephros transgenically expressing the large T protein of polyoma virus under the control of the early viral enhancer. As a tumor suppresser gene with a key role in urogenital development, WT1 is implicated as predisposition gene in the pathogenesis of Wilms' tumour (WT).
Further Information
Research council deposit: Yes
Price_code: C
Bibliographic References:
Cell 1995; 81:391
By Beatrice . . .
TITLE: M15
DATE: 2005/04/24 00:32
URL:http://www.biotech.ist.unige.it/cldb/c13312.html
European Collection of Cell Cultures,
Health Protection Agency, Porton Down, Salisbury, Wiltshire, UK
June Poulton
European Collection of Cell Cultures
Health Protection Agency,
Porton Down
SP40JG Salisbury, Wiltshire UK
Phone: +44-1980-612512
Fax: +44-1980-611315
E-mail: ecacc@hpa.org.uk
URL: http://www.ecacc.org.uk/

The MEF cells (from ICR mice) have been registered as Catalogue No. ATCC#SCRC-1046 in the ATCC. In addition, the MEF cells can be obtained in accordance with the description of the reference (Nagy A, et al. Manipulating The Mouse Embryo: A Laboratory Manual. Third Edition Cold Spring Harbor Press; 2003).

The ST2 cells have been registered as RCB0224 in RIKEN, Tsukuba Institute, BioResource Center. In addition, the ST2 cells can be obtained in accordance with the description of the reference (Ogawa, M., Nishikawa, S., Ikuta, K., Yamamura, F., Naito, M., Takahashi, K. and Nishikawa, S. EMBO J. 1988; 7: 1337-1343).

These feeder cells can be cultured according to ordinary techniques using general media for animal cells supplemented with serum and the like (e.g., RPMI medium and DMEM medium).

In Step (A) of the present invention, methods used for culturing the pluripotent stem cells in the presence of the above-mentioned feeder cells are not particularly limited, and, for example, the above-mentioned feeder cells can be used as feeder cells to co-culture the pluripotent stem cells therewith. Specifically, with a suitable medium containing activin and/or BFGF, the pluripotent stem cells can be inoculated on a plate to which the above-mentioned feeder cells has been plated in advance so as to form monolayer, and thus, the pluripotent stem cells can be co-cultured with them. The co-culture may be carried out for several days whereby differentiation of definitive endoderm cells from the pluripotent stem cells can be achieved.

With regard to a culture medium used in Step (A) of the present invention, any general culture media used for animal cells, such as DMEM medium or RPMI medium, can be used, and activin and/or bFGF can be added to the culture media for use. In addition, the medium used in the step (A) may contain optional components which may be, for example, a serum such as fetal bovine serum; knockout serum replacement (KSR); or glucose, if desired. Furthermore, Activin A is preferably used as activin. The activin concentration in the medium is not particularly limited as long as the concentration can induce the differentiation into definitive endoderm cells. However, the concentration can be 5-300 ng/mL, and preferably 10-200 ng/mL. The bFGF concentration in the medium is not also particularly limited as long as the concentration can induce the differentiation into definitive endoderm cells. However, for example, the concentration is 5-300 ng/mL, and preferably 10-200 ng/mL.

In Step (A) of the present invention, whether or not pluripotent stem cells have been differentiated into definitive endoderm cells can be confirmed by examining expression of the above-mentioned ECD and CXCR4. In addition, if desired, the definitive endoderm cells can also be separated from a culture product obtained in Step (A), and the separated definitive endoderm cells can be subjected to Step (B) of the present invention. Specifically, the definitive endoderm cells can be separated by flow cytometry using fluorescently-labelled antibodies against ECD and CXCR4.

(Induction of Differentiation of Definitive Endoderm Cells into Intestinal Cells)

In Step (B) of the present invention, the definitive endoderm cells obtained in Step (A) are cultured in the presence of (2'Z,3'E)-6-bromoindirubin-3'-oxime (BIO) and N-[(3,5-difluorophenyl)acetyl]-L-Ala-2-phenyl-L-Gly-tert-butyl-OH (DAPT) to thereby induce differentiation of the definitive endoderm cells into intestinal cells. Specifically, when the definitive endoderm cells are cultured in the presence of BIO and DAPT for several days (for example, 1 to 30 days, 1 to 20 days, 1 to 16 days), cells emerge therein, in which expression of marker genes for intestinal cells, such as Cdx2, Ifabp, Isx, Villin 1, Lactase, or Glut 2, can be recognized. That is, Step (B) of the present invention allows induction of differentiation into intestinal cells in which expression of various intestinal cell marker genes can be recognized. The concentration of BIO and DAPT in the medium may be within a range that can induce differentiation of the definitive endoderm cells into intestinal cells, and is not particularly limited. The concentration of BIO in the medium may be, for example, within ranges of 1 to 500 µM, preferably 1 to 100 µM, more preferably 1 to 50 µM, yet more preferably 1 to 20 µM, and yet more preferably 1 to 10 µM. On the other hand, the concentration of DAPT in the medium may be, for example, within ranges of 1 to 500 µM, preferably 1 to 100 µM, more preferably 1 to 50 µM, and yet more preferably 1 to 20 µM. Furthermore, in Step (B), additional substances that activate induction of differentiation of the definitive endoderm cells into intestinal cells can also be added to the culture medium besides BIO and DAPT. As for examples of such substances, a substance which activates the FGF signal transmission system, a substance which activates the BMP signaling, a substance which activates the hedgehog (Hh) signaling and the like can be mentioned. FGF2 can be mentioned as a specific example of the substance which activates the FGF signaling, BMP4 can be mentioned as a specific example of the substance which activates the BMP signaling, and SAG (Smoothened Agonist; N-Methyl-N'-(3-pyridinylbenzyl)-N'-(3-chlorobenzo[b]thiophene-2-carbonyl)-1,4-diaminocyclohexane, $SAG_{1.3}$) can be mentioned as a specific example of the substance which activates the hedgehog (Hh) signaling, respectively. When mouse ES cells are used as a starting material, these substances can particularly promote induction of differentiation of said cells into intestinal cells, and therefore, it is preferable to use these substances when mouse ES cells are used as a starting material, and, in that case, these substances may be used alone or in combination.

Furthermore, in Step (B), it is preferable that the above-mentioned definitive endoderm cells be cultured in the presence of feeder cells of M15 cells or MEF cells. This is because, when the definitive endoderm cells are cultured in the presence of the above-mentioned BIO and DAPT and in the presence of these feeder cells, various types of differentiated intestinal cells that more strongly express the above-mentioned marker genes for intestinal cells can be obtained.

Moreover, intestinal cells produced according to the present invention include cells in which expression of various intestinal cell-type markers such as Tff3 (goblet cell marker), mucin2 (Muc2) (goblet cell marker), DBA (Dolilchos biflorus agglutinin) (goblet cell marker), lysozyme (Paneth cell marker), Sox9 (Paneth cell marker), somatostatin (Sst) (enteroendocrine cell marker), chromogranin A (enteroendocrine cell marker), gastrin (enteroendocrine cell marker), synaptophysin (enteroendocrine cell marker), Sst (enteroendocrine cell marker), and Sct (enteroendocrine cell) can be recognized. That is, the present invention enables production of all the cell types of intestinal cell lineages. Accordingly, in the present invention, after induction of differentiation into intestinal cells is carried out in Step (B), a step may be provided, in which expression of the above-mentioned marker genes for intestinal cells, and/or marker genes for various cell types of intestinal cell lineages is detected in the levels of mRNA and/or protein. With regard to methods used for detecting expression of such marker genes, various known methods such as a RT-PCR method and Western blotting can be adopted. Furthermore, in the method of the present invention, a step in which differentiated intestinal cells or various intestine cells are separated, respectively, by use of various known techniques such as flow cytometry (FACS analysis) may be further provided.

As for types of the culture medium, conditions for culturing definitive endoderm cells, methods for culturing M15 cells or MEF cells, etc. in Step (B), those mentioned for above Step (A) can be adopted.

As described above, according to the production method of the present invention, all the cell types of intestinal cell lineages can be produced, and thus, these various intestinal cells can be utilized in regeneration medicine for diseases such as various digestive-system malignant tumors, ulcerative colitis, and Crohn disease. Additionally, the various intestinal cells produced by the present invention can be used for toxicological tests (safety tests) or drug efficacy/pharmacology tests of pharmaceuticals.

Furthermore, according to the present invention, further provided is a method of screening for substances which promote or inhibit induction of differentiation of pluripotent stem cells into intestinal cells, the method including: culturing pluripotent stem cells in the presence of a test substance in producing intestinal cells by Step (A) inducing differentiation of pluripotent stem cells into definitive endoderm cells and Step (B) culturing the definitive endoderm cells in the presence of BIO and DAPT to thereby induce differentiation of the definitive endoderm cells into intestinal cells; and comparing a level of differentiation of the pluripotent stem cells into intestinal cells in a case where the pluripotent stem cells are cultured in the presence of the test substance with a level of differentiation of pluripotent stem cells into intestinal cells in a case where the pluripotent stem cells are cultured in the absence of the test substance. Growth factors, low-molecular-weight compounds, etc. can be subjected thereto as the test substance. In that case, an amount of maker transcript or a protein thereof expressed in intestinal cells, or both of them can be used as indicators to thereby determine the levels of differentiation into intestinal cells.

The present invention will be described in more detail with reference to the following Examples. However, the present invention is not particularly limited to the following Examples.

EXAMPLES

Example 1

(A) Materials and Methods (1) Cell Lines

In this example, a cell line R1 was used as mouse ES cells. The cell line R1 was maintained on mouse embryonic fibroblast (MEF) feeders in 2000 mg/L-glucose-containing DMEM supplemented with Leukemia Inhibitory Factor (LIF), 10% fetal bovine serum (FBS), 100 µM of non-essential amino acids (NEAA), 2 mM of L-Gln, 50 units/mL of penicillin and 50 µg/mL of streptomycin (PS), and 100 µM β-mercaptoethanol.

The MEF was isolated from a mouse embryo of embryonic day (E) 12.5-14.5.

The mesonephric cell line M15 was those provided by Dr. T. Noce (Keio University) and Dr. M. Rassoulzadegan (University of Nice-Sophia Antipolis, Antipolis, France). The R1 ES cells were those provided by Dr. Andras Nagy. The MEF and M15 cells were treated with mitomycin C (Sigma), and were used as previously reported (Shiraki, N., Higuchi, Y., Harada, S., Umeda, K., Isagawa, T., Aburatani, H., Kume, K. and Kume, S. (2009). Differentiation and characterization of embryonic stem cells into three germ layers. Biochem Biophys Res Commun 381, 694-9; Shiraki, N., Umeda, K., Sakashita, N., Takeya, M., Kume, K. and Kume, S. (2008). Differentiation of mouse and human embryonic stem cells into hepatic lineages. Genes Cells 13, 731-46; Shiraki, N., Yoshida, T., Araki, K., Umezawa, A., Higuchi, Y., Goto, H., Kume, K. and Kume, S. (2008). Guided differentiation of embryonic stem cells into Pdx1-expressing regional-specific definitive endoderm. Stem Cells 26, 874-85).

(2) Intestinal Differentiation of Mouse ES Cells

The ES cells were culture on M15 cells added with 20 ng/mL of activin and 50 ng/mL of bFGF in DMEM medium containing 10% fetal bovine sera and 4500 mg/mL of glucose for 5 days, and were analyzed using flow cytometry for definitive endoderm. For intestinal differentiation, the ES cells were further cultured on M15 or MEF cells, in the presence of BIO and DAPT, or without BIO and DAPT but with FGFs, in media with 10% KSR at a glucose concentration of 2000 mg/mL.

(3) Maintenance of Human ES Cells

Human ES cells (KhES-3) (PMID: 16707099) was those provided by Dr. N. Nakatsuji and Dr. H. Suemori (Kyoto University, Kyoto, Japan), and were used in accordance with the hES cell guidelines of the Japanese government. The undifferentiated hES cells were maintained on a feeder layer of MEF in Knockout DMEM/F12 (Invitrogen) supplemented with 20% KSR, L-Gln, NEAA and β-ME under 3% $CO_2$. To passage the hES cells, hES cell colonies were detached from the feeder layer by treating them with 0.25% trypsin and 0.1 mg/mL of collagenase IV in PBS containing 20% KSR and 1 mM of $CaCl_2$ at 37° C. for 5 minutes, followed by adding a culture medium thereto and gently pipetting them several times to desegregate ES cell clumps into smaller pieces (5-20 cells).

(4) Intestinal Differentiation of Human ES Cells

For differentiation induction, the human ES cells were pre-treated with Y27632 (Wako) for 24 hours, and then, they were plated at 50,000 cells per well in 24-well plates that had been pre-coated with M15 cells. The ES cells were dissociated with 0.25% trypsin-EDTA (Invitrogen), and cultured in Y27632 containing an ES maintenance medium for one day. One day after plating, the cells were washed by PBS, and the medium was changed to a differentiation medium. The cells were cultured in a first differentiation medium [RPMI1640 (Invitrogen) supplemented with 2% B-27 (Invitrogen), NEAA, L-Gln, PS and β-ME] from day 0 to day 10, and then, the medium was switched to a second differentiation medium (DMEM supplemented with 10% KSR, NEAA, L-Gln, PS and β-ME) on day 10, and the cells were cultured up to day 35. Activin A (100 ng/mL) was added thereto during day 0 to day 10 of differentiation, and BIO and DAPT were added during day 10 to day 35. The Medium was replaced every 2 days with a fresh medium supplemented with growth factors.

(5) Growth Factors and Inhibitors

The following concentrations were used unless otherwise specifically indicated:

5 µM of BIO (Calbiochem);
10 µM of DAPT (Peptide Inst.);
20 ng/mL of recombinant human activin-A (R&D Systems); and
10 µg/mL of human bFGF (Peprotech), U0126 (Sigma), LY294002 (Calbiochem), and SU5402 (Calbiochem), respectively;
256 ng/mL of FGF2 (human bFGF) (Peprotech); and
50 ng/mL of FGF4 (Peprotech), FGF5 (Sigma), FGF7 (R&D Systems), FGF8 (Cosmo Bio), FGF9 (Peprotech), FGF10 (R&D Systems) and FGF18 (Sigma), respectively.

(6) Flow cytometry analysis and reculture of sorted cells

The cells were dissociated with Cell Dissociation Buffer (Invitrogen), adjusted to $1 \times 10^6$ cells/50 µL, and stained with appropriate antibodies. A biotin- or Alexa 488-conjugated anti-E-cadherin monoclonal antibody ECCD2, and a phycoerythrin (PE)-conjugated anti-Cxcr4 mAb 2B11 (BD Pharmingen) were used as the antibodies. The stained cells were purified with FACS Aria (BD Pharmingen). Data were recorded using the BD FACSDiva Software program (BD Pharmingen), and were analyzed using the Flowjo program (Tree Star).

(7) Reverse Transcription-Polymerase Chain Reaction (RT-PCR) Analysis

RNA was extracted from the ES cells using TRI Reagent (Sigma) or RNeasy micro-kit (Qiagen), and then, was treated with DNase (Sigma). Three micrograms of RNA were reverse-transcribed using a MMLV reverse transcriptase (Toyobo) and oligo dT primers (Toyobo). The primer sequences and the number of cycles are shown in Table 1. The PCR conditions for each cycle include initial denaturation at 96° C. for one minute, and the second and subsequent cycles of denaturation at 96° C. for 30 seconds, annealing at 60° C. for 2 seconds and extension at 72° C. for 20 seconds, and the final cycle of extension at 72° C. for 7 minutes. RT-PCR products were separated by 5% non-denaturing polyacrylamide gel electrophoresis, stained with SYBR Green I (Molecular Probes), and visualized using Gel Logic 200 Imaging System (Kodak).

TABLE 1

| Mouse Primers | Sequences | Number of Cycles |
|---|---|---|
| Pax8-U | TGCCTTTCCCCATGCTGCCTCCGTGTA (SEQ ID NO: 1) | 27 |
| Pax8-D | GGTGGGTGGTGCGCTTGGCCTTGATGTAG (SEQ ID NO: 2) | |
| Cdx2-U | TGGTGTACACAGACCATCAGC (SEQ ID NO: 3) | 25 |
| Cdx2-D | CCTTGGCTCTGCGGTTCT (SEQ ID NO: 4) | |
| Ifabp-U | GGAAAGGAGCTGATTGCTGTCC (SEQ ID NO: 5) | 25 |
| Ifabp-D | CTTTGACAAGGCTGGAGACCAG (SEQ ID NO: 6) | |

TABLE 1-continued

| | | Number of Cycles |
|---|---|---|
| Isx-U | AGTTTGCCCAGACCACAAAG (SEQ ID NO: 7) | 25 |
| Isx-D | CAGGGTAATGGGTGAAGTGG (SEQ ID NO: 8) | |
| Hoxc8-U | GTCTCCCAGCCTCATGTETC (SEQ ID NO: 9) | 27 |
| Hoxc8-D | TGGAACCAAATCTTCACTTGTC (SEQ ID NO: 10) | |
| Villin-U | GTTATGAGCCCGAAAGTGGA (SEQ ID NO: 11) | 25 |
| Villin-D | AGAGAAGGCAGCTGGAGTCA (SEQ ID NO: 12) | |
| Lactase (Lct)-U | CCCATCTTCAAAAACGGAGA (SEQ ID NO: 13) | 27 |
| Lactase (Lct)-D | CCCTATCGGCATCAAAAGAC (SEQ ID NO: 14) | |
| β-actin-U | GTGATGGTGGGAATGGGTCA (SEQ ID NO: 15) | 18 |
| β-actin-D | TTTGATGTCACGCACGATTTCC (SEQ ID NO: 16) | |
| Tff-3-U | CATCCTGTGCAGTGGTCCT (SEQ ID NO: 17) | 25 |
| Tff-3-D | GCACCATACATTGGCTTGG (SEQ ID NO: 18) | |
| Lysozyme (Lyz1)-U | GAGACCGAAGCACCGACTATG (SEQ ID NO: 19) | 25 |
| Lysozyme (Lyz1)-D | CGGTTTTGACATTGTGTTCGC (SEQ ID NO: 20) | |
| Sst-U | CCGTCAGTTTCTGCAGAAGT (SEQ ID NO: 21) | 23 |
| Sst-D | CAGGGTCAAGTTGAGCATCG (SEQ ID NO: 22) | |
| Secretin (Sct)-U | GTTGCAGCATTTGTCACACC (SEQ ID NO: 23) | 25 |
| Secretin (Sct)-D | TGAACGATCAACAGCAGACC (SEQ ID NO: 24) | |
| Synaptophysin (Syp)-U | GGTTCCGGAGTGGGCAGGTTTG (SEQ ID NO: 25) | 25 |
| Synaptophysin (Syp)-D | GGGGCGTGGGGTGGAATCAG (SEQ ID NO: 26) | |
| Gast-U | ACCAATGAGGACCTGGAACA (SEQ ID NO: 27) | 25 |
| Gast-D | TCCTACTGGTCTTCCTCAGCA (SEQ ID NO: 28) | |
| Cck-U | ATGAAGAGCGGCGTATGTCT (SEQ ID NO: 29) | 25 |
| Cck-D | CGATGGGTATTCGTAGTCCTC (SEQ ID NO: 30) | |

| Human Primers | Sequence | Number of Cycles |
|---|---|---|
| hCDX2-U | GGAACCTGTGCGAGTGGATG (SEQ ID NO: 31) | 25 |
| hCDX2-D | AGGTGGTGGGGCTTGCGGGGCG (SEQ ID NO: 32) | |
| hVILLIN-U | ACTTCTATGGGGCGACTG (SEQ ID NO: 33) | 25 |
| hVILLLN-D | ATGCGTCCCTTGAAGATGG (SEQ ID NO: 34) | |
| hIFABP-U | GATAAACTAAAAGCATAGGCTGCATATG (SEQ ID NO: 35) | 25 |
| hIFABP-D | TCAAAATCAGAATGGCAATTATCTCT (SEQ ID NO: 36) | |
| hISX-U | CAGGAGGCTCTGAGAGGACA (SEQ ID NO: 37) | 25 |
| hISX-D | ATCTGTGCAGAAGGGATGCT (SEQ ID NO: 38) | |
| hLCT-U | GCTGCACCGTTAGAGATGAC (SEQ ID NO: 39) | 25 |
| hLCT-D | CGGTTTTTGCTCCCTTAACA (SEQ ID NO: 40) | |
| hTFF3-U | CCCAAGGAGTGCAACAACC (SEQ ID NO: 41) | 25 |
| hTFF3-D | GGGACAGAAAAGCTGAGATGA (SEQ ID NO: 42) | |
| hLYZ-U | GATGGCTACAGGGGAATCAG (SEQ ID NO: 43) | 25 |
| hLYZ-D | TAACTGCTCCTGGGGTTTTG (SEQ ID NO: 44) | |
| hGAST-U | TGGCTGGAGGAAGAAGAAGA (SEQ ID NO: 45) | 25 |
| hGAST-D | TCAGTTTTTCAGGGGACAGG (SEQ ID NO: 46) | |
| hSYP-U | CTCCACTCCTCCCAACTCTG (SEQ ID NO: 47) | 25 |
| hSYP-D | ACTCCACACCTCCTCTCCAA (SEQ ID NO: 48) | |
| hSST-U | GATGCTGTCCTGCCGCCTCC (SEQ ID NO: 49) | 25 |
| hSST-D | TGCCATAGCCGGGTTTGA (SEQ ID NO: 50) | |
| hFOXA2-U | GCAGATACCTCCTACTACCA (SEQ ID NO: 51) | 25 |
| hFOXA2-D | GAAGCAGGAGTCTACACAGT (SEQ ID NO: 52) | |

TABLE 1-continued

| | | |
|---|---|---|
| hGAPDH-U | CGAGATCCCTCCAAAATCAA (SEQ ID NO: 53) | 27 |
| hGAPDH-D | CATGAGTCCTTCCACGATACCAA (SEQ ID NO: 54) | |
| | 96° C. 1 min | |
| | 96° C. 30 sec | |
| | 60° C. 2 sec | |
| | 72° C. 20 sec | |
| | 72° C. 7 min | |
| | 4° C- | |

(8) Antibodies

The antibodies used herein are as follows.
mouse anti-Cdx2 (BioGenex, San Ramon, Calif.);
rat anti-mouse E-cadherin (TaKaRa BIO INC., Japan);
goat anti-HNF4a (Santa cruz Biotechnology Inc);
mouse anti-Villin (BD Transduction Laboratories);
rabbit anti-Lysozyme (Diagnostic Biosystems);
rabbit anti-Chromogranin A (Epitomics, Inc.,);
biotin-conjugated Dolichos biflorus agglutinin (DBA) lectin (SIGMA);
goat anti-somatostatin (Santa cruz Biotechnology Inc);
mouse anti-Muc2 (visionbiosystems novocastra);
rabbit anti-Sox9 (Millipore);
rabbit anti-Claudin-7 (Abcam); and
rabbit anti-Glut-2 (Chemicon).

(9) Alkaline Phosphatase Activity Measurement

The cultured cells were fixed in 4% paraformaldehyde for 10 min. After washing the with Phosphate buffered saline containing 0.1% Tween-20 (TBST) for 20 minutes, a coloring reaction was carried out with 35 μg/mL of nitroblue tetrazolium (NBT) and 17.5 μg/mL of 5-bromo-4-chloro-3-indolyl phosphate in NTMT (100 mM Tris-HCl [pH 9.5], 100 mM of NaCl, 50 mM of $MgCl_2$, 0.1% Tween-20, 2 mM of levamisole).

(10) PAS Staining and Alucian Blue Staining

The cultured cells were fixed in 4% paraformaldehyde for 10 minutes. PAS staining solution (Muto Pure Chemicals, Tokyo, Japan) or Alucian blue 8GX (SIGMA) were used according to the manufacturer's instructions.

(B) Results (1) Activation of the Canonical Wnt Signaling and Inhibition of Notch Signaling Potentiate Intestinal Differentiation of ES Cells on M15 Cells.

The present inventors have shown previously that, when ES cells were cultured on M15 cells, the ES cells were differentiated into a definitive endoderm fate, and then, differentiated into various cell types of definitive endodermal lineages [including Caudal type homeobox2 (Cdx2)-expressing intestinal cells]. Cdx2 is one type of intestine-specific transcription factor, and is useful as a marker gene for intestinal cells [Silberg, D. G., Swain, G. P., Suh, E. R. and Traber, P. G. (2000). Cdx1 and cdx2 expression during intestinal development. Gastroenterology 119, 961-71].

In an attempt to investigate an optimal condition for differentiation of the definitive endoderm into intestinal cell lineages, several culture conditions were tested by addition of chemicals to the ES cell culture after definitive endoderm cells were induced (FIG. 1A). By assaying them with a quantitative PCR, it was found that addition of (2'Z,3'E)-6-bromoindrirubin-3'-oxime (BIO) (a GSK-3β inhibitor or an activator of the canonical Wnt signaling) or (3,5-Difluoroohenylacetyl)-Ala-Phg-OBu' (DAPT) (a gamma-secretase inhibitor that functions as an inhibitor of the Notch signaling) induced expression of Intestinal fatty acid binding protein (Ifabp) on Day 20 (d20) of the differentiation (FIG. 1B). The intestinal fatty acid binding protein (Ifabp) is useful as a gene marker for intestinal cells [Green, R. P., Cohn, S. M., Sacchettini, J. C., Jackson, K. E. and Gordon, J. I. (1992). The mouse intestinal fatty acid binding protein gene: nucleotide sequence, pattern of developmental and regional expression, and proposed structure of its protein product. *DNA Cell Biol* 11, 31-41]. Moreover, it was found that simultaneous addition of BIO and DAPT dramatically increased expression of Cdx2 and Ifabp (FIGS. 1B and 1C). Temporal expression of various intestinal markers in the ES cells cultured on M15 cells in the presence of BIO and DAPT was examined (FIG. 1D). Expression of Villin1 (Villin) [Maunoury, R., Robine, S., Pringault, E., Leonard, N., Gaillard, J. A. and Louvard, D. (1992). Developmental regulation of villin gene expression in the epithelial cell lineages of mouse digestive and urogenital tracts. *Development* 115, 717-28] was induced on d5, and expression of Cdx2 was induced at a substantial level on d10 of the differentiation. Furthermore, induction of Ifabp was recognized on Day 15; and expression of Lactase (Lct) [Bosse, T., Fialkovich, J. J., Piaseckyj, C. M., Beuling, E., Broekman, H., Grand, R. J., Montgomery, R. K. and Krasinski, S. D. (2007). Gata4 and Hnflalpha are partially required for the expression of specific intestinal genes during development. *Am J Physiol Gastrointest Liver Physiol* 292, G1302-14] and intestine specific homeobox (Isx) [Choi, M. Y., Romer, A. I., Hu, M., Lepourcelet, M., Mechoor, A., Yesilaltay, A., Krieger, M., Gray, P. A. and Shivdasani, R. A. (2006). A dynamic expression survey identifies transcription factors relevant in mouse digestive tract development. *Development* 133, 4119-29] was recognized on Day 20. In consistency with the RT-PCR analysis, the immunohistochemistry analysis of Cdx2 expression showed that a high proportion of ES cells be turned into Cdx2-expressing cells in the presence of BIO and DAPT.

(2) Addition of BIO and DAPT Posterizes the Definitive Endoderm.

Figure 2:
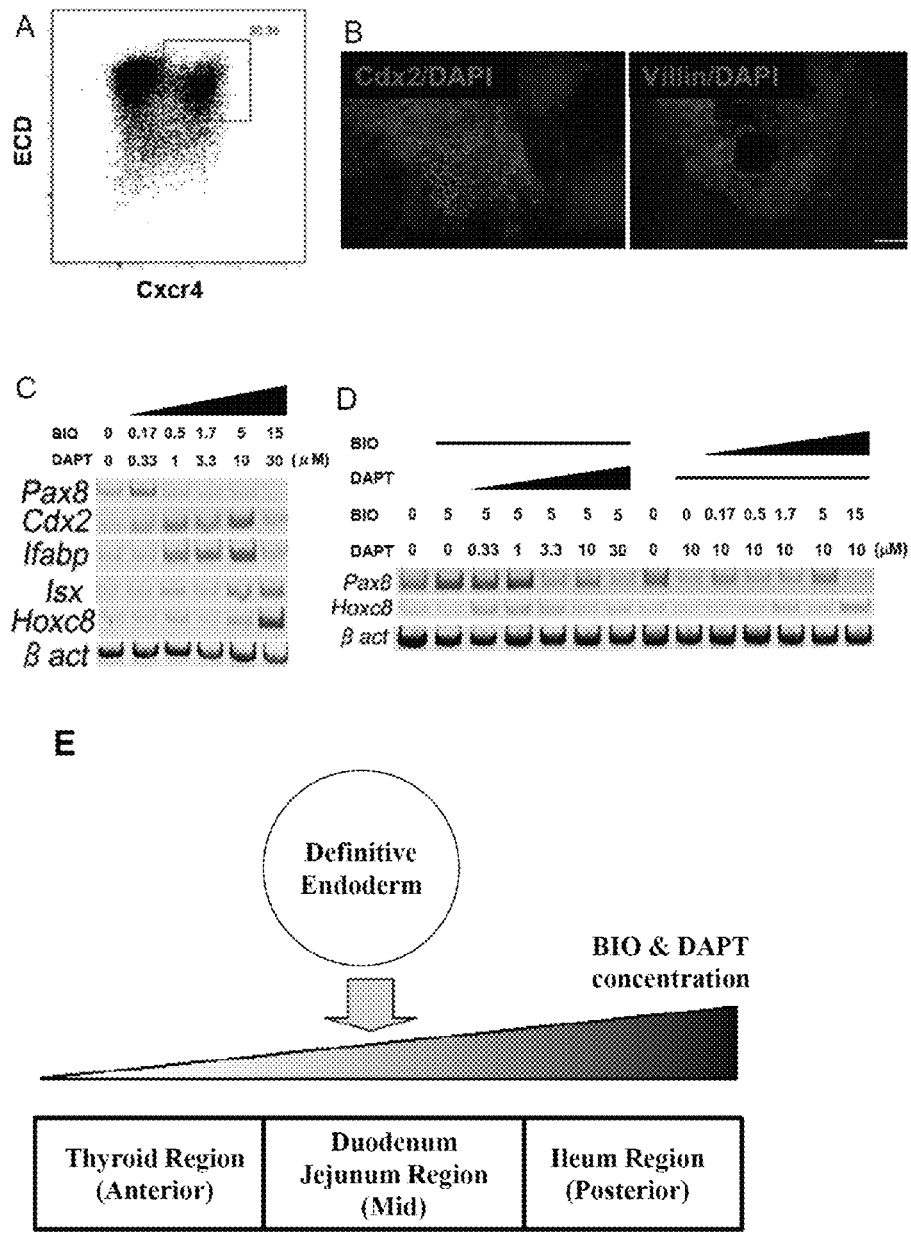
FIG. 2A shows results in which definitive endoderm (Cxcr4+/ECD+) cells (square) were sorted from the ES cells at day 4, which had been cultured on M15 cells in the presence of BIO and DAPT, with flow cytometry.
FIG. 2B shows results in which the definitive endoderm cells were re-cultured on M15 cells, and expression of Cdx2 and villin was analyzed with respect to the cells after 11 days re-culture (equivalent to the day 15 cells). These cells were differentiated into Cdx2-expressing cells (left) and villin-expressing intestinal cells (right).
FIG. 2C shows results in which expression patterns of a panel of markers indicative of anterior-to-posterior identities are examined to evaluate effects of BIO and DAPT in patterning the definitive endoderm. When BIO and DAPT were not added, or added at low concentration, anterior marker Pax8 was induced. Cdx2 and Ifabp were induced at a moderate concentration of BIO and DAPT (1/30-1). Hoxc8 (posterior marker) was expressed only when BIO and DAPT were added at high concentrations.
FIG. 2D shows results in which effects of BIO and DAPT addition on the expressions of Pax8 and Hoxc8 were tested. Hoxc8 (posterior marker) was induced at a high concentration of BIO.
FIG. 2E is a schematic representation of a working hypothesis of intestinal regionalization by a graded concentrations of BIO and DAPT.

To examine whether the induced intestinal cells were of a definitive endoderm origin, the definitive endoderm was recovered by flow cytometry on Day 4 of the differentiation (FIG. 2A), and the cells were re-cultured until Day 15. The definitive endoderm cells were further differentiated into Cdx2- or villin-expressing intestinal cells upon addition of BIO and DAPT (FIG. 2B). This result revealed that the Cdx2- and villin-expressing intestinal cells were of a definitive endoderm origin.

Next, effects of graded concentrations of BIO and DAPT on expression of a panel of markers indicative of region specific anterior-to-posterior markers were tested. Expression of Pared box gene 8 (Pax8) [Mansouri, A., Chowdhury, K. and Gruss, P. (1998). Follicular cells of the thyroid gland require Pax8 gene function. *Nat Genet.* 19, 87-90], an anterior marker for thyroid differentiation, was recognized when BIO and DAPT were not added, or added at low concentrations. Cdx2 and Ifabp were induced at moderate concentrations of BIO and DAPT. Isx and Homeobox C8 (Hoxc8) [Kawazoe, Y., Sekimoto, T., Araki, M., Takagi, K., Araki, K. and Yamamura, K. (2002). Region-specific gastrointestinal Hox code during murine embryonal gut development. *Dev Growth Differ* 44, 77-84] were induced at high concentrations of BIO and DAPT (FIG. 2C). These results suggested that intestinal regionalization be specified by graded concentrations of BIO and DAPT.

Next, the ES cells were further treated with BIO (5 µM) or DAPT (10 µM), and effects of the graded concentrations of the other (either BIO or DAPT) on expressions of Pax8 and Hoxc8 were tested. In the presence of BIO (5 µM), the high concentration of DAPT turned off the anterior marker Pax8 while inducing the posterior marker Hoxc8 (FIG. 2D). Meanwhile, when the ES cells were treated with DAPT (10 µM) and the graded concentrations of BIO, the high BIO concentration turned off Pax8 while turning on Hoxc8. These results demonstrate that, when the Notch signaling is inhibited, an activation of the canonical signaling by BIO inhibits the anterior differentiation of the definitive endoderm, and enhanced the posterior differentiation of the same (FIG. 2E).

(3) MEF is More Potent than M15 Cells in Inducing ES Cell Differentiation into Intestinal Lineages in the Presence of BIO and DAPT.

Figure 3:
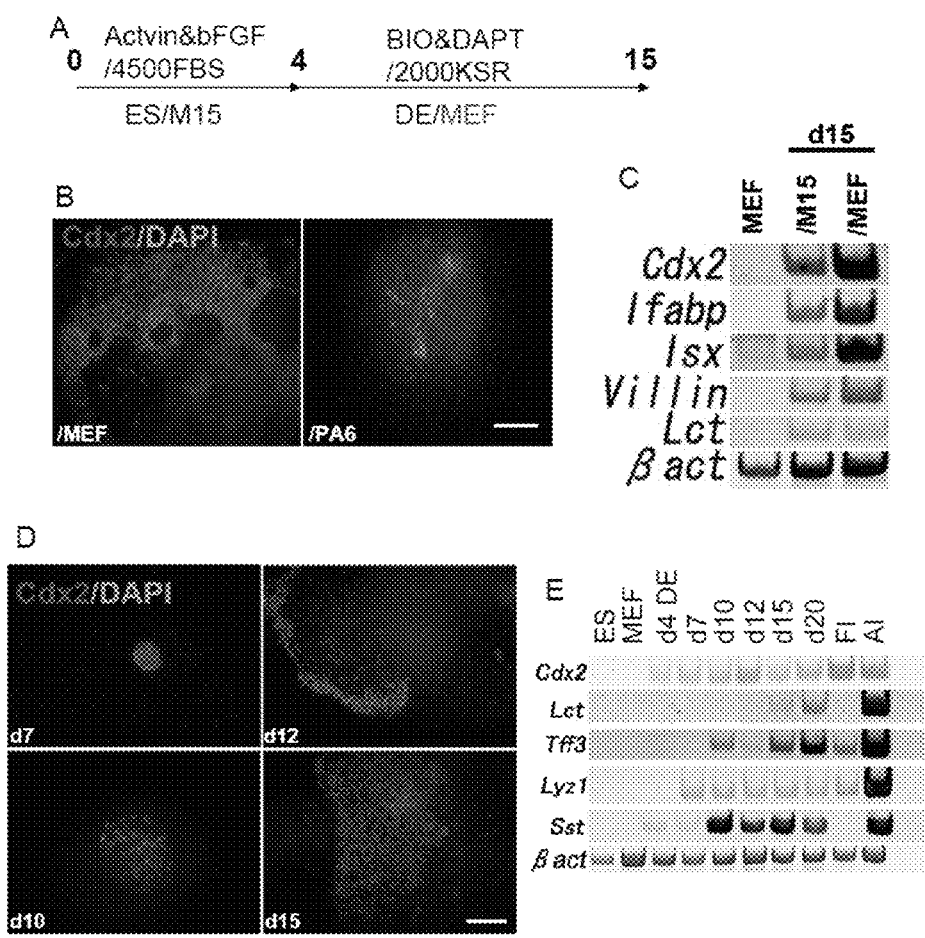
FIG. 3A is a schematic representation showing an outline of the experiment. ES cells were differentiated on M15 for 4 days. On day 4, definitive endoderm cells were isolated, and then, were re-plated on MEF cells, and were cultured in the presence of BIO and DAPT.
FIG. 3B shows results in which, after the ES cell-derived definitive endoderm cells were re-cultured on MEF cells or PA6 cells instead of M15 cells, expression of Cdx2 in the cells were examined. When the definitive endoderm cells were re-cultured on MEF cells, differentiated cells expressing Cdx2 were observed.
FIG. 3C show results in which expression of various intestinal markers was analyzed with respect to the definitive endoderm cells which had been cultured on M15 or MEF cells. It was shown that Cdx2, Ifabp, Isx, Villin and lactase (lct) be induced in the definitive endoderm cells cultured on M15 or MEF cells.
FIG. 3D shows results of time-course analysis of Cdx2-expressing cells appearance upon culturing on MEF cells. Cdx2-expressing cells are observed at a substantial amount from day 12 of differentiation on MEF cells.
FIG. 3E shows results of time-course analysis on expression of various intestinal markers. The time when the differentiation initiates is defined as day 0. Tff3 is a goblet cell marker; Lysozyme (Lyz1) is a Paneth cell marker; and Sst is an enteroendocrine marker.

Next, culturing the definitive endoderm on MEF cells or PA6 cells was compared to M15 cells, whereby effects of intestinal differentiation were tested with respect to each of the feeder cells. Definitive endoderm cells were obtained by culturing ES cells on M15 cells in the presence of activin and bFGF for 4 days, and then, they were sorted by flow cytometry. The sorted definitive endoderm cells were re-cultured in the presence of BIO and DAPT on M15 cells, MEF cells or PA6 cells until Day 15 (FIG. 3A). Cdx2-expressing differentiated cells were also observed when MEF cells used, but such differentiated cells were not recognized when PA6 cells were used (FIG. 3B). RT-PCR analysis showed that an even stronger expression of intestinal markers induced when they were grown on MEF cells, compared to M15 cells (FIG. 3C). The expression of Cdx2 can be detected at a high level from Day 12 of the differentiation (FIG. 3D). Other markers, such as Trefoil factor 3 (Tff3, a goblet cell marker); Lysozyme (Lyz1, a Paneth cell marker); Somatostatin (Sst, an enteroendocrine marker); and Lct were also detected from Day 12 or Day 15 (FIG. 3E) [Hocker, M. and Wiedenmann, B. (1998). Molecular mechanisms of enteroendocrine differentiation. *Ann N Y Acad Sci* 859, 160-74; Schonhoff, S. E., Giel-Moloney, M. and Leiter, A. B. (2004). Minireview: Development and differentiation of gut endocrine cells. *Endocrinology* 145, 2639-44].

(4) Characterization of the Intestinal Cells Derived from ES Cells

Figure 4:
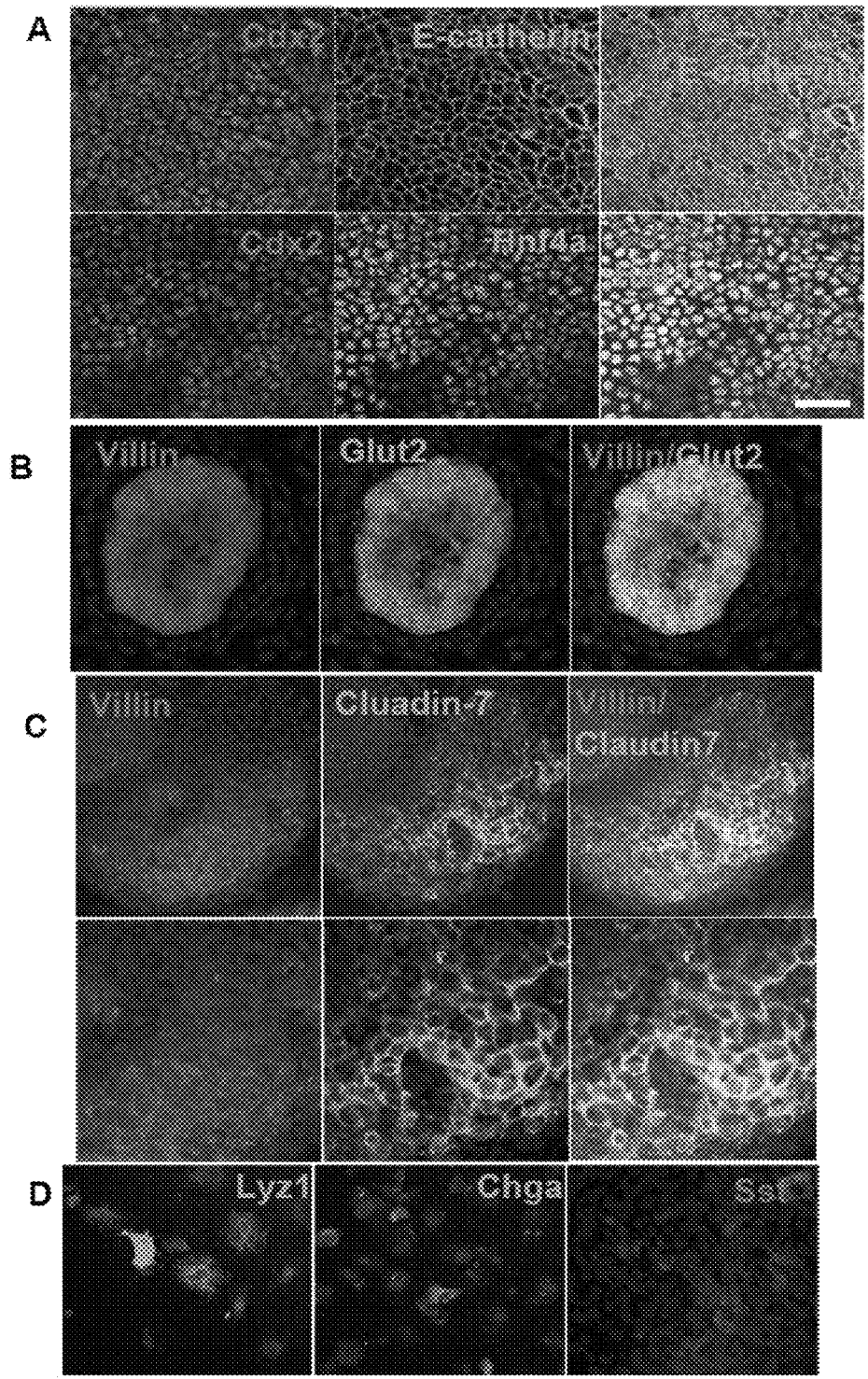
FIG. 4 shows results in which expression of various markers was examined with respect to the ES cells which had been subjected to differentiation on MEF cells.
Figure 5:
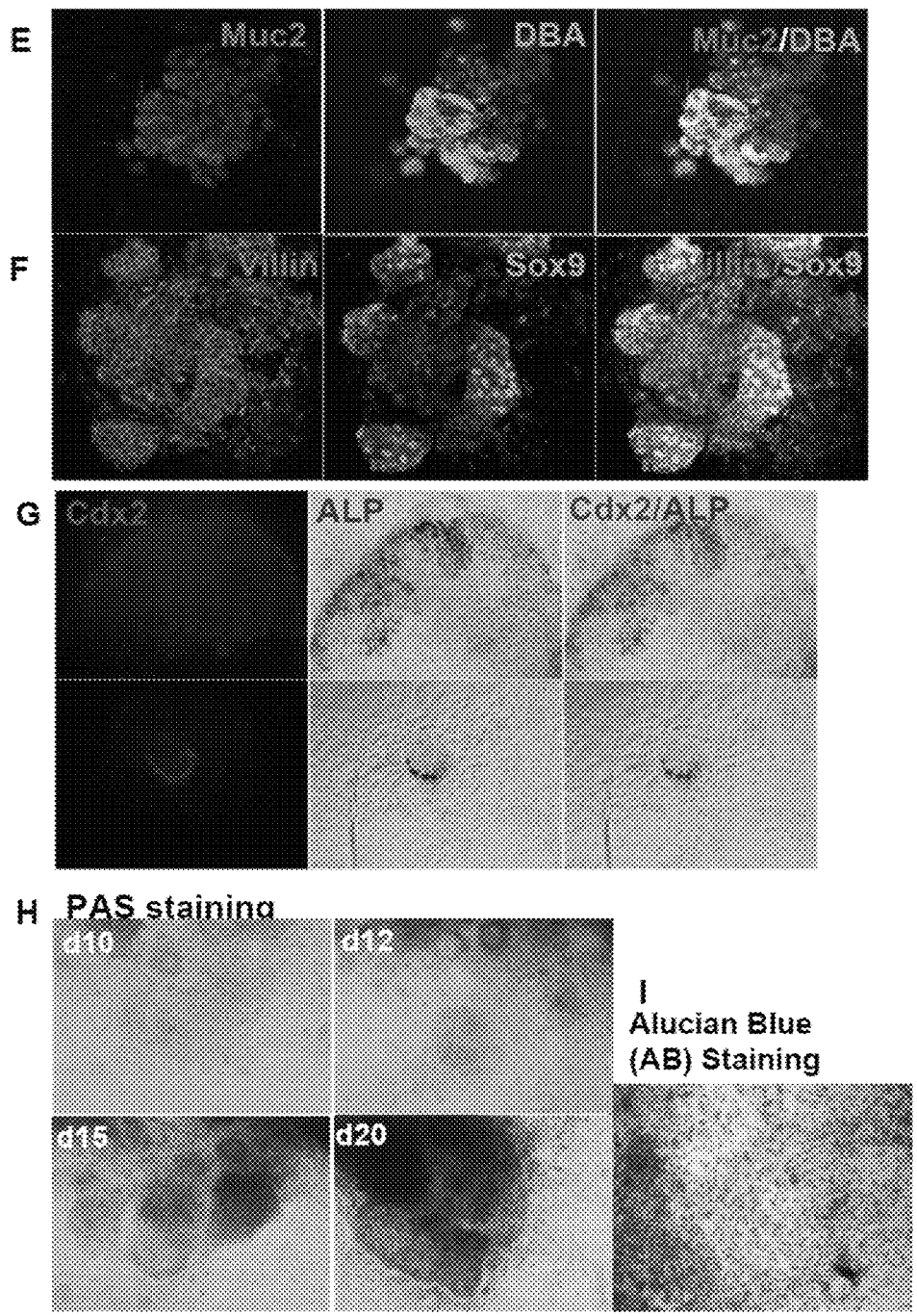
FIG. 5 results in which expression of various markers was examined with respect to the ES cells which had been subjected to differentiation on MEF cells (FIGS. 5E and 5F) or M15 cells (FIGS. 5G to GI).

Next, types of intestinal cells differentiated from ES cells were investigated. Cdx2-expressing intestinal cells are epithelium cells which are indicated by expression of E-cadherin (epithelial marker) [Lugo-Martinez, V. H., Petit, C. S., Fouquet, S., Le Beyec, J., Chambaz, J., Pincon-Raymond, M., Cardot, P. and Thenet, S. (2009). Epidermal growth factor receptor is involved in enterocyte anoikis through the dismantling of E-cadherin-mediated junctions. *Am J Physiol Gastrointest Liver Physiol* 296, G235-44]. The Cdx2-expressing cells also co-express Hepatic nuclear factor 4 alpha (HNF4a) (endoderm marker) [Cattin, A. L., Le Beyec, J., Barreau, F., Saint-Just, S., Houllier, A., Gonzalez, F. J., Robine, S., Pincon-Raymond, M., Cardot, P., Lacasa, M. et al. (2009). Hepatocyte nuclear factor 4alpha, a key factor for homeostasis, cell architecture, and barrier function of the adult intestinal epithelium. *Mol Cell Biol* 29, 6294-308], and Glut2 (enterocyte marker) [Gouyon, F., Caillaud, L., Carriere, V., Klein, C., Dalet, V., Citadelle, D., Kellett, G. L., Thorens, B., Leturque, A. and Brot-Laroche, E. (2003). Simple-sugar meals target GLUT2 at enterocyte apical membranes to improve sugar absorption: a study in GLUT2-null mice. *J Physiol* 552, 823-32], or Claudin7 (tight junction marker) [Fujita, H., Chiba, H., Yokozaki, H., Sakai, N., Sugimoto, K., Wada, T., Kojima, T., Yamashita, T. and Sawada, N. (2006). Differential expression and subcellular localization of claudin-7, -8, -12, -13, and -15 along the mouse intestine. *J Histochem Cytochem* 54, 933-44] (FIGS. 4A-4C). Furthermore, other markers were also examined. Paneth cells (Lysozyme expression), and cells expressing endocrine markers, such as ChromograninA and Somatostatin, were induced (FIG. 4D). These cells also expressed mucin2 [van Klinken, B. J., Einerhand, A. W., Duits, L. A., Makkink, M. K., Tytgat, K. M., Renes, I. B., Verburg, M., Buller, H. A. and Dekker, J. (1999). Gastrointestinal expression and partial cDNA cloning of murine Muc2. *Am J Physiol* 276, G115-24] and lectin DBA (Dolichos biflorus agglutinin) (goblet cell makers) [Kandori, H., Hirayama, K., Takeda, M. and Doi, K. (1996). Histochemical, lectin-histochemical and morphometrical characteristics of intestinal goblet cells of germfree and conventional mice. *Exp Anim* 45, 155-60], and a transcription factor Sox9 (Paneth cell marker) [Mori-Akiyama, Y., van den Born, M., van Es, J. H., Hamilton, S. R., Adams, H. P., Zhang, J., Clevers, H. and de Crombrugghe, B. (2007). SOX9 is required for the differentiation of Paneth cells in the intestinal epithelium. *Gastroenterology* 133, 539-46], and these were also detected in the differentiated ES cells (FIGS. 5E and 5F). Enterocytes were characterized by alkaline phosphatase activities (FIG. 5G). Goblet cells were characterized by being positive for PAS (FIG. 4H) and Alucian blue staining (FIG. 5I). These characteristics are all confirmed in the ES cell-derived intestinal cells generated in the culture of this example. These results indicate that ES cells be induced to differentiate into all cell types of intestinal cell lineages (including absorptive cells of enterocytes and secretory cells of Paneth cells, goblet cells and endocrine cells).

(5) Differentiation of Human ES Cells into Intestinal Cells are Potentiated by Activation of the Canonical Wnt Signaling and Inhibition of the Notch Signaling.

Figure 6:
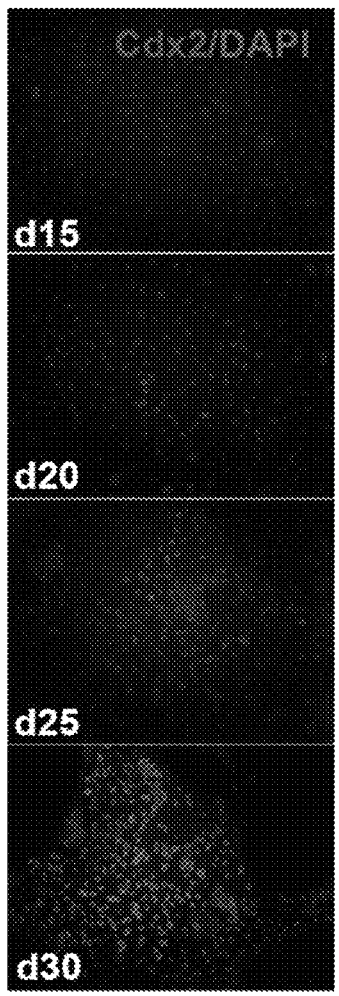
FIG. 6A shows results in which intestinal cells expressing Cdx2 were induced from human ES cells khES-3 in the presence of BIO and DAPT on M15 cells on day 25, using similar procedures.
FIG. 6B shows results of time-course analysis by RT-PCR on expression of various intestinal markers. Intestinal markers Cdx2 and Villin; enterocyte markers Ifabp and Isx; a goblet cell marker Tff3; a Paneth cell marker Lysozyme (Lyz1); and enteroendocrine markers Sst, Sct, Syp, Sst and Gast were expressed in the khES-3 cells which had been subjected to differentiation in the presence of BIO and DAPT and on M15 cells.
FIGS. 6C and 6D shows that differentiated khES-3 cells showed alkaline phosphatase activities (C), and were positive for PAS staining (D).
Figure 6:
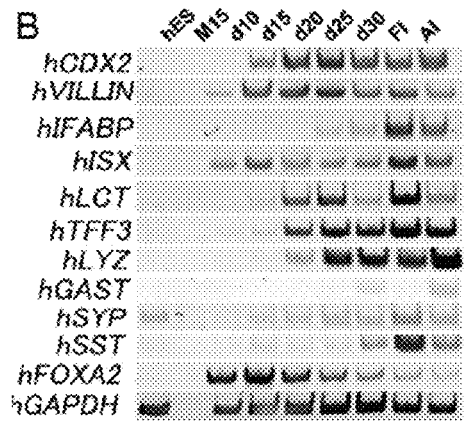
Figure 6:
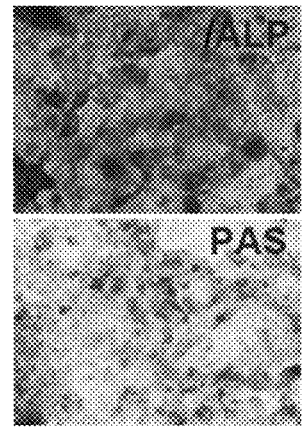
Figure 6:
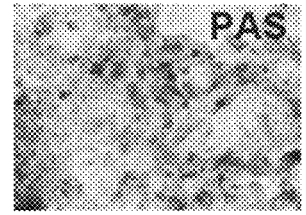

Next, it was examined whether or not human ES cells could also be directed into intestinal cells by addition of BIO and DAPT, in the same manner as mouse ES cells. In this experiment, khES-3 (human ES cell line) [Suemori, H., Yasuchika, K., Hasegawa, K., Fujioka, T., Tsuneyoshi, N. and Nakatsuji, N. (2006). Efficient establishment of human embryonic stem cell lines and long-term maintenance with stable karyotype by enzymatic bulk passage. *Biochem Biophys Res Commun* 345, 926-32] was used. After culturing KhES-3 with activin at 100 µM for 10 days, khES-3 differentiated into definitive endoderm. Then, BIO and DAPT were added to the KhES-3 culture, and this was continuously cultured until Day 35. Then, this was assayed by immunohistochemistry or RT- PCR. khES-3 expressing Cdx2 was detected by immunohistochemistry at Day 25 (FIG. 6A) and RT-PCR at an early stage of Day 15 (FIG. 6B). In the RT-PCR, molecular markers for enterocytes (hVillin, hIfabp, hIsx); goblet cells (hTff3) [Suemori, S., Lynch-Devaney, K. and Podolsky, D. K. (1991). Identification and characterization of rat intestinal trefoil factor: tissue- and cell-specific member of the trefoil protein family. Proc Natl Acad Sci USA 88, 11017-21]; Paneth cells (hLyz) [Ouellette, A. J. (1997). Paneth cells and innate immunity in the crypt microenvironment. Gastroenterology 113, 1779-84]; and endocrine cells (Gastrin, hGast; Synaptophysin, hSyp; Somatostain, hSst) [Hocker, M. and Wiedenmann, B. (1998). Molecular mechanisms of enteroendocrine differentiation. Ann N Y Acad Sci 859, 160-74; Schonhoff, S. E., Giel-Moloney, M. and Leiter, A. B. (2004). Minireview: Development and differentiation of gut endocrine cells. Endocrinology 145, 2639-44] were also detected, and thus, it was revealed that expression of these molecular markers be induced (FIG. 6B). Differentiated khES-3 cells were positive for PAS staining, indicating that functional Goblet cells were derived.

(6) ES Cell Differentiation into Intestinal Lineages is Potentiated by the FGF Signaling, which is Mediated Through PI3K but not MAPK.

It has been already publicly known that M15 cells and MEF cells both express a substantial level of FGF2 (bFGF). Therefore, next, effects of FGF2 (bFGF) on intestinal differentiation were tested. Definitive endoderm cells recovered by flow cytometry were re-cultured in the presence of FGF2 (bFGF) instead of BIO and DAPT. The RT-PCR analysis demonstrated that, when they were cultured in the presence of BIO and DAPT, molecular markers for enterocytes (Ifabp, Isx), goblet cells (Tff3), Paneth cells (Lyz1) and enteroendocrine cells [Sct (Gouyon, F., Caillaud, L., Carriere, V., Klein, C., Dalet, V., Citadelle, D., Kellett, G. L., Thorens, B., Leturque, A. and Brot-Laroche, E. (2003). Simple-sugar meals target GLUT2 at enterocyte apical membranes to improve sugar absorption: a study in GLUT2-null mice. J Physiol 552, 823-32), Syp, Sst, Gast] were expressed. However, when they were cultured only in the presence of FGF2, without BIO and DAPT, these markers were induced at much lower levels. Therefore, simultaneous addition of BIO and DAPT is more potent than FGF2 (bFGF) in inducing most differentiated markers of intestinal cells, with the exception of Cholecystokinin (Cck) (FIG. 7A).

Next, effects of various FGFs were tested by way of adding the various FGFs to the ES cell culture from Day 4 of the differentiation. Addition of FGF2 (bFGF) induced Cdx2-expressing intestinal cells. FGF4 was more potent in inducing Cdx2-expressing cells than FGF2 (bFGF). FGF 7, 9, 10 and 18 also induced intestinal differentiation of ES cells, but the levels thereof were lower (FIG. 7B). However, addition of these FGFs is not so potent as addition of BIO and DAPT in intestinal differentiation. This result is consistent with FIG. 7A.

Next, relationships between BIO, DAPT and the FGF signaling were investigated. An antagonist of FGF receptor "SU5402" and an inhibitor of PI3K "LY294002" were used therefor. The blockade of FGF signaling by SU5402 or the blockade of PI3K by LY294002 partially inhibited the intestinal differentiation which was mediated by BIO and DAPT (FIGS. 7C and 7D). These results demonstrated that the FGF signaling, particularly through PI3K, functions cooperatively with the Wnt and Notch signaling to mediate intestinal differentiation.

(C) Discussion

In the intestinal epithelium, intestinal stem cells (ISCs) and progenitor cells present in the crypts proliferate vigorously, and provide differentiated cells. There are four types of non-proliferative, terminally differentiated epithelial cells, such as enterocytes, goblet cells and enteroendocrine cells, which reside in the villi, and Paneth cells, which are located in the crypt base [Barker, N., van de Wetering, M. and Clevers, H. (2008). The intestinal stem cell. Genes Dev 22, 1856-641.

Figure 7:
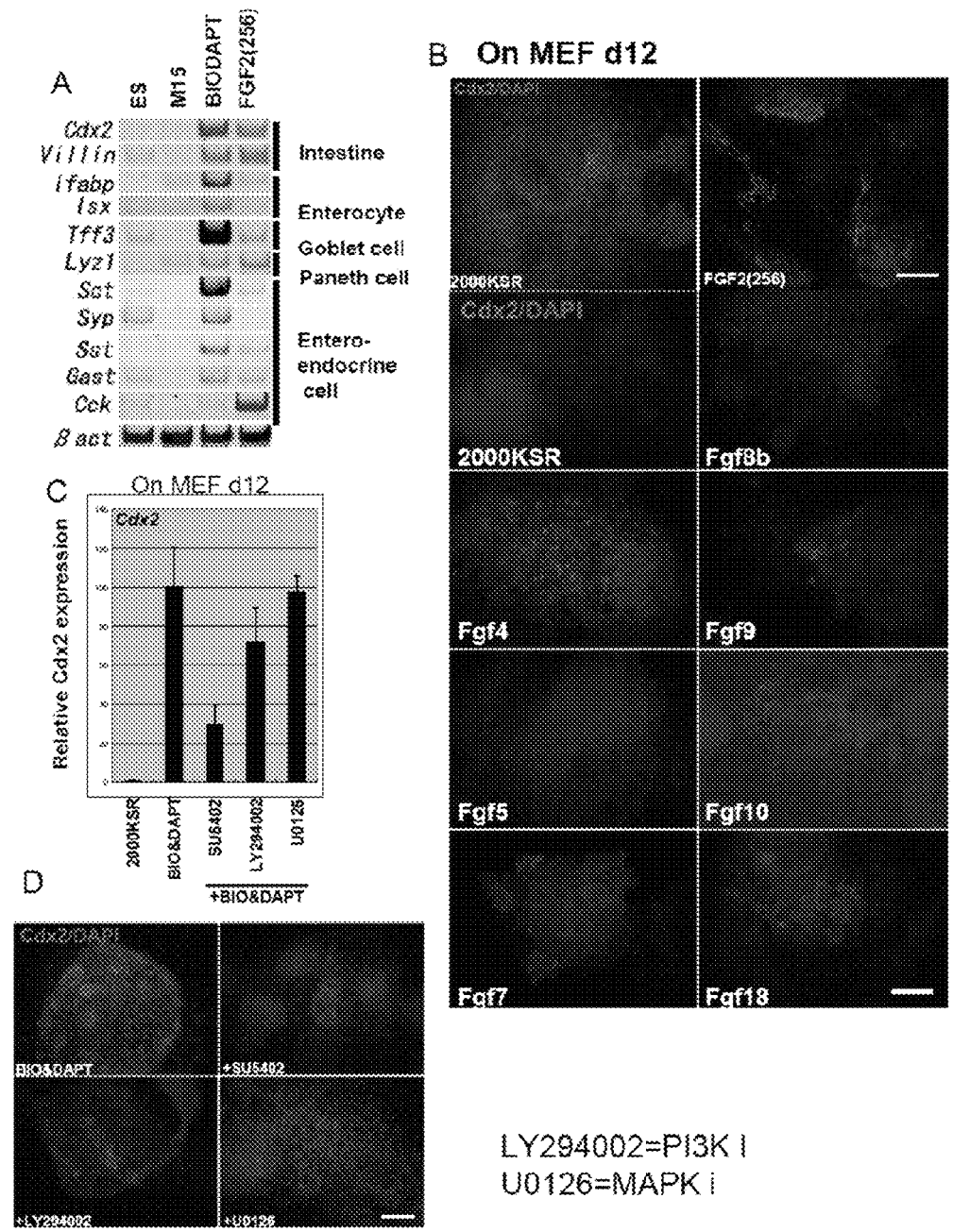
FIG. 7A shows results in which those obtained by adding BIO and DAPT to ES cells differentiated on M15 were compared with those obtained by adding FGF2 (bEGF) to the same ES cells with respect to various markers. Addition of BIO and DAPT induced differentiated cell types of enterocytes, goblet cells, Paneth cells and enteroendocrine cells from the ES cells. 256 ng/mL of FGF2 (bEGF) instead of BIO and DAPT induced intestine differentiation, but it can be realized that expression of differentiated cell markers be small in extent.
FIG. 7B results in which effects of various FGFs on definitive endoderms were examined. Definitive endoderms were sorted from ES cells which had been cultured on M15 cells with activin and bFGF for 4 days, and the sorted cells were re-plated on MEF cells. FGF4, FGF5, FGF7, FGF8b, FGF9, FGF10 and FGF18 were added thereto, and their potentials to enhance ES cell differentiation into Cdx2-expressing intestinal cells were examined.
FIGS. 7C and 7D shows results in which effects of SU5402 (FGF receptor antagonist), LY29402 (PI3K inhibitor), and U0126 (MAPK inhibitor) on the effects of addition of BIO and DAPT were examined. The intestinal differentiation from ES cells by BIO and DAPT was partially inhibited by SU5402 (FGF receptor antagonist) and LY29402 (PI3K inhibitor), but was not inhibited by U0126 (MAPK inhibitor).

In this Example, the ES-cell-derived definitive endoderm cells were cultured on M15 cells or MEF cells, whereby it was confirmed that activation of the canonical Wnt signaling pathways by addition of BIO, and inhibition of the Notch pathway by addition of DAPT, simultaneously induced the gut endoderm to express the posterior markers, and enhanced intestinal differentiation. Fgf emitted from M15 and MEF cells assists the establishment of intestinal characters (FIG. 7). Therefore, the results of this Example indicate that the FGF, Wnt and Notch signaling function cooperatively to promote differentiation of ES cells into the intestinal lineages.

It has been known that a FGF involves in specification of the human ES cell-derived definitive endoderm into different fore gut lineages in a dosage-dependent manner [Ameri, J., Stahlberg, A., Pedersen, J., Johansson, J. K., Johannesson, M. M., Artner, I. and Semb, H. (2010). FGF2 specifies hESC-derived definitive endoderm into foregut/midgut cell lineages in a concentration-dependent manner. Stem Cells 28, 45-56]. It has been known that, at high FGF2 levels, specification of midgut endoderm into small intestinal progenitors is increased at the expense of Pdx1+ pancreatic progenitors (the above reference of Ameri et al.).

It has been also reported that the canonical Wnt pathway activates proliferation of immature cells in the crypt and maturation of Paneth cells [van Es, J. H., Jay, P., Gregorieff, A., van Gijn, M. E., Jonkheer, S., Hatzis, P., Thiele, A., van den Born, M., Begthel, H., Brabletz, T. et al. (2005a). Wnt signalling induces maturation of Paneth cells in intestinal crypts. Nat Cell Biol 7, 381-6]. Moreover, activation of the Notch signaling is capable of amplifying the intestinal progenitor pool while inhibiting the goblet and enteroendocrine cell differentiation [Zecchini, V., Domaschenz, R., Winton, D. and Jones, P. (2005). Notch signaling regulates the differentiation of post-mitotic intestinal epithelial cells. Genes Dev 19, 1686-91]. Furthermore, after conditional removal of the common Notch pathway transcription factor CSL/RBP-J, a rapid, massive conversion of proliferative crypt cells into post-mitotic goblet cells has been observed (van Es, J. H., van Gijn, M. E., Riccio, O., van den Born, M., Vooijs, M., Begthel, H., Cozijnsen, M., Robine, S., Winton, D. J., Radtke, F. et al. (2005b). Notch/gamma-secretase inhibition turns proliferative cells in intestinal crypts and adenomas into goblet cells. Nature 435, 959-63). Additionally, it has been known that a similar phenotype was obtained by blocking the Notch cascade with a gamma-secretase inhibitor (the above reference of van Es et al.).

Thus, maintenance of undifferentiated, proliferative cells in crypts and adenomas requires the concerted activation of the Notch and Wnt cascades.

Example 2

Example 2 shows cases in which inhibitors or activators against various signal transduction systems were further added besides BIO and DAPT in the method of the present invention.

(1) Test Example 1

Addition of Various Inhibitors

In order to clarify what mechanism induces the intestinal differentiation in a case where mouse ES cells are used as a starting material, inhibitors against various signal transduction systems were added besides BIO and DAPT, and conditions in which expression of an intestinal marker Cdx2 decreases were evaluated.

As an inhibitor, 500 ng/mL of Noggin (R&D systems) or 200 nM of Dorsomorphin (SIGMA-ALDRICH), which is a BMP-signaling inhibitor; 1 µM of LE540 (Wako), which is a retinoic-acid-signaling inhibitor; 250 nM of KAAD-Cyclopamine (Calbiochem), which is a hedgehog-signaling inhibitor; or 10 µM of AMD3100 (SIGMA-ALDRICH), which is a Cxcr4 inhibitor, was added thereto. In the same manner as Example 1, the mouse ES cells were differentiated into definitive endoderm cells on M15 cells, and then, the definitive endoderm cells were sorted by flow cytometry, and were re-cultured on MEF cells. After that, the above-sorted definitive endoderm cells were cultured in the presence of BIO (5 µM) and DAPT (10 µM) as well as the above-mentioned inhibitor for 8 days (until the 12th day of cultivation) in accordance with the method described in Example 1, RNAs were extracted from the cells by the method described in Example 1, and expression of the Cdx2 gene, namely an intestinal marker, was analyzed by real-time PCR. The real-time PCR was carried out by use of the primer pairs used in Example 1 (see Table 1), Thunderbird SYBR qPCR mix (Toyobo), and 7500 Fast Real-Time PCR system (ABI Company). The PCR reaction cycles are shown in Table 1. The results are shown in FIG. 8A.

As a result, addition of Noggin, Dorsomorphin, or KAAD-Cyclopamine lowered expression of Cdx2. That is, it was suggested that the BMP signaling and Hedgehog (Hh) signaling upregulate the intestinal differentiation in a case in where mouse ES cells are used as a starting material.

(2) Test Example 2

Addition of Various Activators

The above-described experiment using inhibitors revealed that the FGF signaling (experiment by addition of SU5402) and the BMP signaling as well as the Hh signaling involve in the differentiation into intestine.

Therefore, next, an experiment in which the FGF signaling, the BMP signaling and the Hh signaling were activated was carried out. In view of micro-array data showing that MEF cells express FGF2 and BMP4, 50 ng/mL of FGF2 (PEPROTECH) and 25 ng/mL of BMP4 (R&D Systems) were used to activate the FGF signaling and the BMP signaling. Furthermore, as to activation of the Hh signaling, 300 nM of SAG (MERCK) (smoothend agonist; smo) was used.

For the experiment of inducing the differentiation, the induction of differentiation was carried out in a feeder-free system as described below. First, mouse ES cells were plated on a gelatin-coated dish at 6,900 cells/cm$^2$. The ES cells were cultured for 7 days in DMEM medium (Dulbecco's Modified Eagle Medium) (Invitrogen, Glasgow, UK) containing 4,500 mg/L of glucose, supplemented with NEAA, L-Gln, PS, β-ME, 10 µg/mL of Insulin (Sigma-Aldrich), 5.5 Kg/mL of Transferin (Sigma-Aldrich), 6.7 pg/mL of Selenium (Sigma-Aldrich), 0.25% AlbuMax (Invitrogen), and 10 ng/mL of recombinant human activin A (R&D Systems, Minneapolis, Minn.), and then, the culture medium was replaced with 10% KSR containing 2,000 mg/mL of glucose, BIO (5 µM) and DAPT (10 µM) and further supplemented with the activator or growth factor. After that, cell culturing was further continued, the cells were separated on the 10th day and the 15th day of cultivation as described in Example 1, and then, the proportion of Cdx2-positive cells was evaluated by use of flow cytometry. The flow cytometry (FACS) analysis was carried out using BD Cytofix/Cytoperm™ Kit (BD Biosciences) in accordance with a manual provided by the manufacturer. The results are shown in FIG. 8B.

Figure 8:
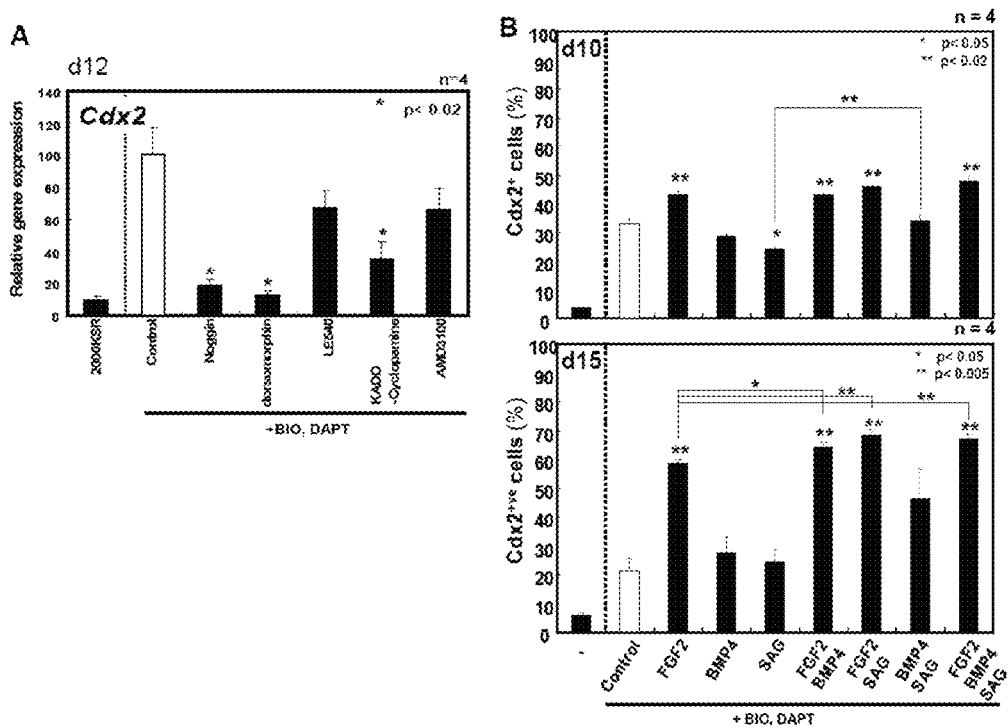
FIG. 8 is a diagram showing results of Test Examples 1 and 2 in Example 2.

As shown in FIG. 8, on the 10th day of cultivation, about 30% of the control cells (with addition of only BIO and DAPT) were Cdx2-positive. In contrast, Cdx2-positive cells reached 40% in that supplemented with FGF2, and thus, an significant increase in the number of Cdx2-positive cells was recognized. Furthermore, addition of SAG (Smoothened Agonist) resulted in a decrease in the number of Cdx2-positive cells, but this was improved by addition of BMP4. On the 15th day of cultivation, about 20% of the control cells were Cdx2-positive. Meanwhile, in the case supplemented with FGF2, about 60% of the cells were Cdx2-positive in the same manner as mentioned above, and thus, it was shown that the cells more efficiently differentiate in that case. Furthermore, it was revealed that the cells yet more efficiently differentiate by addition of BMP4 or SAG besides FGF2. According to the results, it was revealed that FGF2 acts to promote differentiation of mouse ES cells into intestine, and that the BMP signaling or the Hh signaling is activated by BMP4 or SAG in the latter period of cultivation to thereby further promote the differentiation.

(3) Test Example 3

Addition of Various Activators in Human ES Cells

With respect to human ES cells, it was examined whether or not addition of FGF2, BMP4 and/or SAG improves an efficiency of differentiation into Cdx2-positive cells in a feeder-free system.

Figure 9:
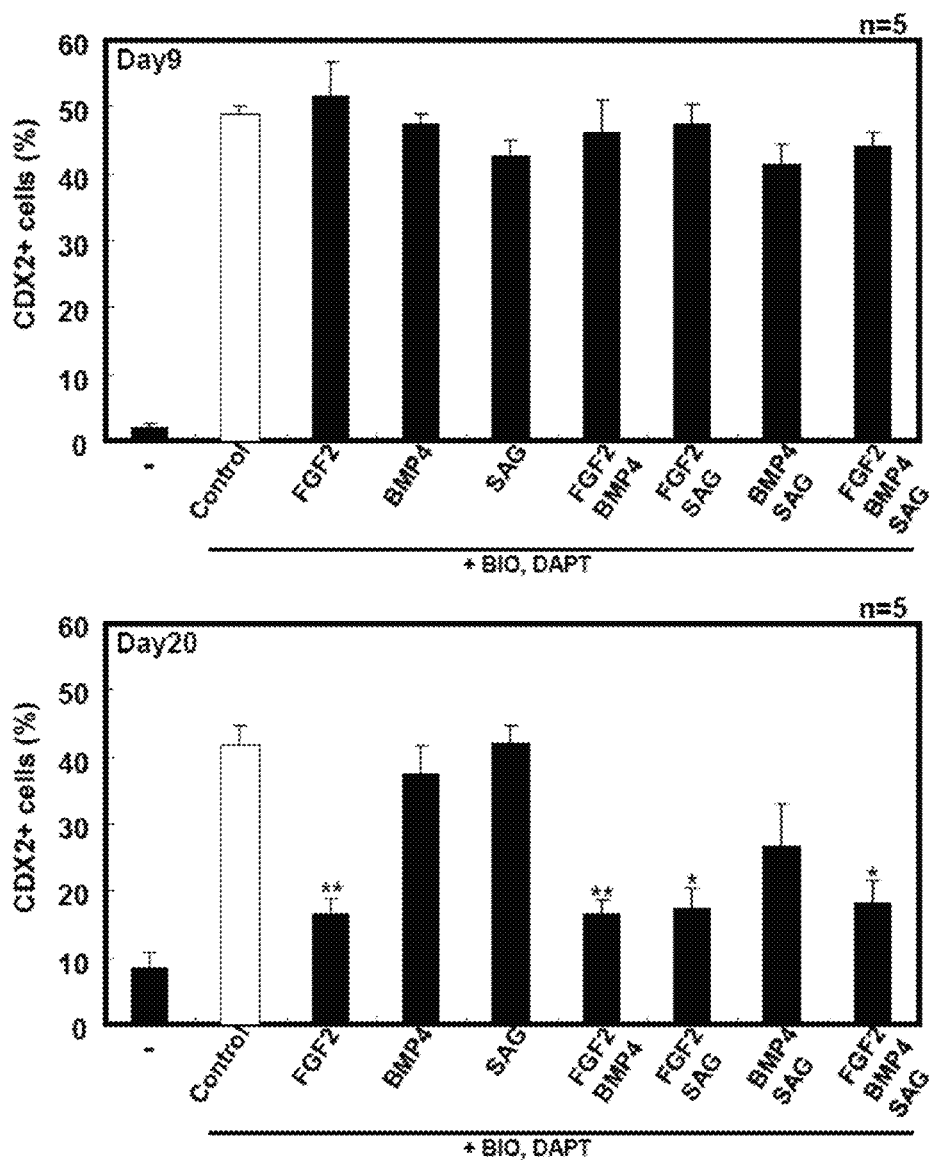
FIG. 9 is a diagram showing results of Test Example 3 in Example 2.

First, for the experiment of inducing the differentiation, human ES cells were plated on gelatin-coated dishes at 69,000 cells/cm$^2$. The ES cells were cultured for seven days in RPMI 1640 medium (Invitrogen) supplemented with NEAA, L-Gln, PS, β-ME, 10 µg/mL of Insulin (Sigma-Aldrich), 100 ng/mL of recombinant human activin A (R&D Systems, Minneapolis, Minn.), and B27 supplement (Invitrogen). Then, the culture medium was replaced with 10% KSR supplemented with 2,000 mg/mL of glucose, BIO (5 ηM), DAPT (10 µM) and activators and growth factors at the concentrations as described in Test Example 2. After that, cell culturing was further continued, and the cells were separated on the 9th day and the 20th day of cultivation in the same manner as Example 1, and then, the proportion of Cdx2-positive cells was evaluated by use of flow cytometry. The flow cytometry (FACS) analysis was carried out using BD Cytofix/Cytoperm™ Kit (BD Biosciences) in accordance with a manual provided by the manufacturer. The results are shown in FIG. 9.

On the 9th day of cultivation, there was no difference among all the conditions, but, on the 20th day of cultivation, the proportion of Cdx2-positive cells decreased in the case supplemented with FGF2. The results suggested that the FGF signaling acts to suppress differentiation of human ES cells into intestine, and that the mechanism for differentiation into intestine in human ES cells is different from that in mouse ES cells.

(4) Test Example 4

Effect of FGF2 Concentration on Human ES Cells

Since there has been a previous report that a high concentration of FGF2 is important for differentiation of human ES cells into Cdx2-positive cells, it was examined whether or not the same results can be obtained. The final concentration of 250 ng/mL of FGF2 was used. In accordance with the method in Test Example 3, differentiation of human ES cells was carried out on gelatin-coated dishes until they differentiated into endoderm, and then (on the 7th day of cultivation), 0, 50, and 250 ng/mL of FGF2, respectively, were added thereto besides BIO (5 μM) and DAPT (10 μM), and the cells were further cultured until the 9th day or 20th day, and the proportion of Cdx2-positive cells was evaluated by flow cytometry. The flow cytometry (FACS) analysis was carried out using BD Cytofix/Cytoperm™ Kit (BD Biosciences) in accordance with a manual provided by the manufacturer. The results are shown in FIG. 10.

Figure 10:
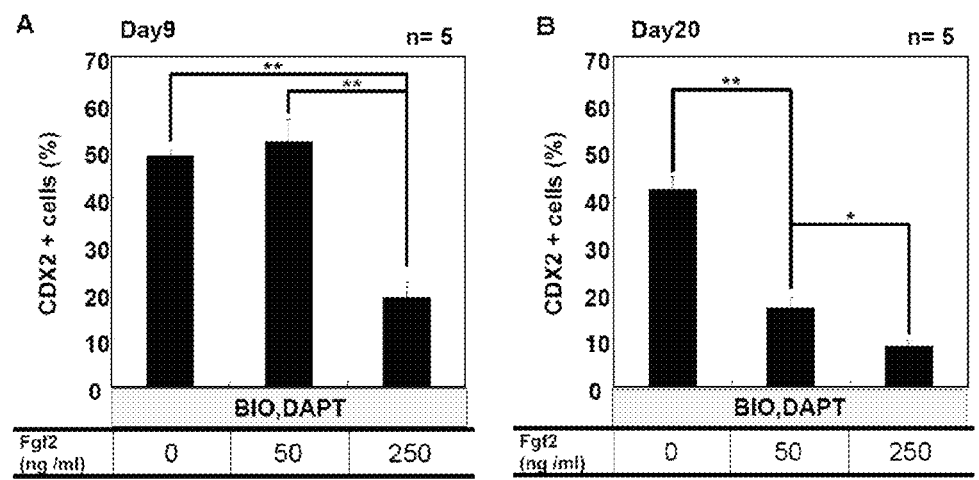
FIG. 10 is a diagram showing results of Test Example 4 in Example 2.

As shown in FIG. 10, it was confirmed that the proportion of Cdx2-positive cells decreased on the 9th day of cultivation in the case supplemented with 250 ng/mL of FGF2 (FIG. 10A). Furthermore, on the 20th day of cultivation, the proportion of Cdx2 positive cells decreased depending on the concentration of FGF2 (FIG. 10B). The results correlated with the results as shown in FIG. 9, and it was further confirmed that FGF2 acts to suppress the differentiation into intestine in the latter period (during the 9 to 20th day) of induction of differentiation.

According to the results of the present Examples, it was demonstrated that manipulation of the FGF-, Wnt-, BMP-, Hh-, and Notch-signal transduction systems allows differentiation into types of functional, mature intestinal cells. In view of these findings, it is evident that the present invention has high industrial applicability in the fields of developmental biology and regeneration medicine.

The invention claimed is:

1. A method of producing intestinal cells expressing Cdx2, comprising the steps of:
   (a) obtaining mouse or human embryonic stem (ES) cells,
   (b) culturing the ES cells of step (a) with Activin and/or bFGF to produce definitive endoderm cells,
   (c) culturing the definitive endoderm cells of step (b) with (2'Z,3'E)-6-bromoindirubin-3'-oxime (BIO) and N-[(3,5-difluorophenyl)acetyl]-L-Ala-2-phenyl-L-Gly-tert-butyl-OH (DAPT) and in the presence of M15 cells or MEF cells, to thereby induce differentiation of the definitive endoderm cells into intestinal cells expressing Cdx2.

2. The method according to claim 1, wherein the definitive endoderm cells are separated from a cell culture obtained in step (b) by flow cytometry using fluorescently-labelled antibodies against E-cadherin (ECD) and CXCR4, and said separated definitive endoderm cells are used in the step (c).

3. The method according to claim 1, wherein the ES cells are cultured in the presence of feeder cells.

4. The method according to claim 3, wherein the feeder cells are cells derived from a mesoderm.

* * * * *